(12) United States Patent
O'Brien et al.

(10) Patent No.: US 8,666,505 B2
(45) Date of Patent: Mar. 4, 2014

(54) WAFER-SCALE PACKAGE INCLUDING POWER SOURCE

(75) Inventors: Richard J. O'Brien, Hugo, MN (US); John K. Day, Chandler, AZ (US); Paul F. Gerrish, Phoenix, AZ (US); Michael F. Mattes, Chandler, AZ (US); David A. Ruben, Mesa, AZ (US); Malcolm K. Grief, Phoenix, AZ (US)

(73) Assignee: Medtronic, Inc., Minneapolis, MN (US)

( * ) Notice: Subject to any disclaimer, the term of this patent is extended or adjusted under 35 U.S.C. 154(b) by 181 days.

(21) Appl. No.: 13/016,253

(22) Filed: Jan. 28, 2011

(65) Prior Publication Data

US 2012/0101540 A1    Apr. 26, 2012

Related U.S. Application Data

(60) Provisional application No. 61/406,961, filed on Oct. 26, 2010.

(51) Int. Cl.
*A61N 1/05* (2006.01)
(52) U.S. Cl.
USPC .......... 607/115; 607/1; 607/2; 607/9; 607/36; 438/25
(58) Field of Classification Search
USPC ............................ 607/1–2, 9, 36, 115; 438/25
See application file for complete search history.

(56) References Cited

U.S. PATENT DOCUMENTS

| | | | |
|---|---|---|---|
| 3,388,301 A | 6/1968 | James | |
| 3,943,557 A | 3/1976 | Frazee et al. | |
| 4,224,565 A | 9/1980 | Sosniak et al. | |
| 4,285,002 A | 8/1981 | Campbell | |
| 4,530,029 A | 7/1985 | Beristain | |
| 4,684,884 A | 8/1987 | Soderlund | |
| 4,701,826 A | 10/1987 | Mikkor | |
| 4,773,972 A | 9/1988 | Mikkor | |
| 4,775,831 A | 10/1988 | Annamalai | |
| 4,810,318 A | 3/1989 | Haisma et al. | |

(Continued)

FOREIGN PATENT DOCUMENTS

| | | |
|---|---|---|
| EP | 0232935 A1 | 8/1987 |
| EP | 1 128 174 A2 | 8/2001 |

(Continued)

OTHER PUBLICATIONS

Wiemer et al., "Developments trends in the field of wafer bonding technologies," 214th ECS Meeting, Abstract #2229, Oct. 12-17, 2008, Honolulu, HI (1 p.).

(Continued)

*Primary Examiner* — Deborah Malamud
(74) *Attorney, Agent, or Firm* — Evans M. Mburu

(57) ABSTRACT

A medical device includes a first substrate, a second substrate, a control module, and an energy storage device. The first substrate includes at least one of a first semiconductor material and a first insulating material. The second substrate includes at least one of a second semiconductor material and a second insulating material. The second substrate is bonded to the first substrate such that the first and second substrates define an enclosed cavity between the first and second substrates. The control module is disposed within the enclosed cavity. The control module is configured to at least one of determine a physiological parameter of a patient and deliver electrical stimulation to the patient. The energy storage device is disposed within the cavity and is configured to supply power to the control module.

20 Claims, 15 Drawing Sheets

(56) References Cited

U.S. PATENT DOCUMENTS

| | | |
|---|---|---|
| 4,868,712 A | 9/1989 | Woodman |
| 4,870,224 A | 9/1989 | Smith et al. |
| 5,054,683 A | 10/1991 | Haisma et al. |
| 5,059,899 A | 10/1991 | Farnworth et al. |
| 5,315,486 A | 5/1994 | Fillion et al. |
| 5,381,039 A | 1/1995 | Morrison |
| 5,381,804 A | 1/1995 | Shambroom |
| 5,489,321 A | 2/1996 | Tracy et al. |
| 5,572,065 A | 11/1996 | Burns |
| 5,592,391 A | 1/1997 | Muyshondt et al. |
| 5,606,264 A | 2/1997 | Licari et al. |
| 5,647,932 A | 7/1997 | Taguchi et al. |
| 5,682,065 A | 10/1997 | Farnworth et al. |
| 5,693,111 A | 12/1997 | Kadowaki et al. |
| 5,837,562 A | 11/1998 | Cho |
| 5,938,956 A | 8/1999 | Hembree et al. |
| 5,955,789 A | 9/1999 | Vendramin |
| 6,022,787 A | 2/2000 | Ma |
| 6,032,064 A | 2/2000 | Devlin et al. |
| 6,074,891 A | 6/2000 | Staller |
| 6,144,866 A | 11/2000 | Miesel et al. |
| 6,145,384 A | 11/2000 | Ikeda et al. |
| 6,171,252 B1 | 1/2001 | Roberts |
| 6,221,024 B1 | 4/2001 | Miesel |
| 6,278,379 B1 | 8/2001 | Allen et al. |
| 6,287,256 B1 | 9/2001 | Park et al. |
| 6,297,072 B1 | 10/2001 | Tilmans et al. |
| 6,297,551 B1 | 10/2001 | Dudderar et al. |
| 6,298,255 B1 | 10/2001 | Cordero et al. |
| 6,303,977 B1 | 10/2001 | Schroen et al. |
| 6,323,550 B1 | 11/2001 | Martin et al. |
| 6,335,669 B1 | 1/2002 | Miyazaki et al. |
| 6,343,019 B1 | 1/2002 | Jiang et al. |
| 6,394,953 B1 | 5/2002 | Devlin et al. |
| 6,477,901 B1 | 11/2002 | Tadigadapa et al. |
| 6,486,534 B1 | 11/2002 | Sridharan et al. |
| 6,500,694 B1 | 12/2002 | Enquist |
| 6,514,798 B2 | 2/2003 | Farnworth |
| 6,515,870 B1 | 2/2003 | Skinner et al. |
| 6,516,808 B2 | 2/2003 | Schulman |
| 6,555,025 B1 | 4/2003 | Krupetsky et al. |
| 6,555,856 B1 | 4/2003 | Staller |
| 6,563,133 B1 | 5/2003 | Tong |
| 6,566,596 B1 | 5/2003 | Askew |
| 6,566,736 B1 | 5/2003 | Ogawa et al. |
| 6,638,784 B2 | 10/2003 | Bartlett et al. |
| 6,696,369 B2 | 2/2004 | Fraser et al. |
| 6,718,206 B2 | 4/2004 | Casavant |
| 6,762,072 B2 | 7/2004 | Lutz |
| 6,774,327 B1 | 8/2004 | Wong |
| 6,821,342 B2 | 11/2004 | Mattes et al. |
| 6,822,326 B2 | 11/2004 | Enquist et al. |
| 6,855,115 B2 | 2/2005 | Fonseca et al. |
| 6,867,073 B1 | 3/2005 | Enquist |
| 6,874,367 B2 | 4/2005 | Jakobsen et al. |
| 6,902,987 B1 | 6/2005 | Tong et al. |
| 6,903,918 B1 | 6/2005 | Brennan |
| 6,962,835 B2 | 11/2005 | Tong et al. |
| 6,968,743 B2 | 11/2005 | Rich et al. |
| 6,986,965 B2 | 1/2006 | Jenson et al. |
| 7,041,178 B2 | 5/2006 | Tong et al. |
| 7,078,726 B2 | 7/2006 | Pichler et al. |
| 7,096,580 B2 | 8/2006 | Gonzalez et al. |
| 7,109,092 B2 | 9/2006 | Tong |
| 7,126,212 B2 | 10/2006 | Enquist et al. |
| 7,147,604 B1 | 12/2006 | Allen et al. |
| 7,150,195 B2 | 12/2006 | Jacobsen et al. |
| 7,162,926 B1 | 1/2007 | Guziak et al. |
| 7,205,181 B1 | 4/2007 | MacIntyre |
| 7,233,048 B2 | 6/2007 | Rybnicek |
| 7,238,999 B2 | 7/2007 | LaFond et al. |
| 7,247,517 B2 | 7/2007 | Rumer et al. |
| 7,305,889 B2 | 12/2007 | Fortin et al. |
| 7,318,264 B2 | 1/2008 | Schugt |
| 7,396,698 B2 | 7/2008 | Horning et al. |
| 7,403,818 B2 | 7/2008 | Kramer et al. |
| 7,417,307 B2 | 8/2008 | Haluzak et al. |
| 7,462,552 B2 | 12/2008 | Tong et al. |
| 7,485,968 B2 | 2/2009 | Enquist et al. |
| 7,495,462 B2 | 2/2009 | Hua et al. |
| 7,540,188 B2 | 6/2009 | Wiese et al. |
| 7,540,934 B2 | 6/2009 | Hofmann et al. |
| 7,553,582 B2 | 6/2009 | Bates |
| 7,563,692 B2 | 7/2009 | Fortin et al. |
| 7,622,324 B2 | 11/2009 | Enquist et al. |
| 7,647,836 B2 | 1/2010 | O'Brien et al. |
| 7,748,277 B2 | 7/2010 | O'Brien et al. |
| 7,759,774 B2 | 7/2010 | Fraser et al. |
| 7,781,250 B2 | 8/2010 | Wang et al. |
| 7,829,363 B2 | 11/2010 | You |
| 7,886,608 B2 | 2/2011 | Mothilal et al. |
| 7,902,851 B2 | 3/2011 | Fenner et al. |
| 8,072,056 B2 | 12/2011 | Mueller et al. |
| 8,125,146 B2 | 2/2012 | Park |
| 8,448,468 B2 | 5/2013 | Pastel et al. |
| 2001/0033024 A1 | 10/2001 | Fraser et al. |
| 2002/0115920 A1 | 8/2002 | Rich et al. |
| 2004/0012083 A1 | 1/2004 | Farrell et al. |
| 2004/0079277 A1 | 4/2004 | Mattes et al. |
| 2004/0082145 A1 | 4/2004 | Reichenbach et al. |
| 2004/0186396 A1 | 9/2004 | Roy et al. |
| 2004/0222478 A1 | 11/2004 | Zhang et al. |
| 2005/0009246 A1 | 1/2005 | Enquist et al. |
| 2005/0065565 A1 | 3/2005 | Kramer et al. |
| 2005/0151151 A1 | 7/2005 | Hawtof et al. |
| 2005/0284815 A1 | 12/2005 | Sparks et al. |
| 2006/0033204 A1 | 2/2006 | Fraser et al. |
| 2006/0110854 A1 | 5/2006 | Horning et al. |
| 2006/0264004 A1 | 11/2006 | Tong et al. |
| 2006/0267167 A1 | 11/2006 | McCain |
| 2006/0273430 A1 | 12/2006 | Hua et al. |
| 2007/0037379 A1 | 2/2007 | Enquist et al. |
| 2007/0107524 A1 | 5/2007 | O'Brien |
| 2007/0158769 A1 | 7/2007 | You |
| 2007/0170839 A1 | 7/2007 | Choi et al. |
| 2007/0179545 A1 | 8/2007 | Warkentin et al. |
| 2007/0199385 A1 | 8/2007 | O'Brien et al. |
| 2007/0251338 A1 | 11/2007 | Wiese et al. |
| 2007/0261497 A1 | 11/2007 | O'Brien et al. |
| 2007/0269921 A1 | 11/2007 | You |
| 2008/0027332 A1 | 1/2008 | Bradley |
| 2008/0102096 A1 | 5/2008 | Molin et al. |
| 2008/0312726 A1 | 12/2008 | Frank et al. |
| 2009/0057868 A1 | 3/2009 | Wang et al. |
| 2009/0270707 A1 | 10/2009 | Alfoqaha et al. |
| 2009/0308169 A1 | 12/2009 | Mothilal et al. |
| 2010/0262208 A1 | 10/2010 | Parker |
| 2010/0263794 A1 | 10/2010 | George et al. |
| 2010/0304151 A1 | 12/2010 | Tuennermann et al. |
| 2010/0314149 A1 | 12/2010 | Gerrish et al. |
| 2010/0314726 A1 | 12/2010 | Mueller et al. |
| 2010/0314733 A1 | 12/2010 | Mueller et al. |
| 2010/0315110 A1 | 12/2010 | Fenner et al. |
| 2010/0324614 A1 | 12/2010 | Mattes et al. |
| 2012/0064670 A1 | 3/2012 | Mueller et al. |
| 2012/0197155 A1 | 8/2012 | Mattes et al. |

FOREIGN PATENT DOCUMENTS

| | | |
|---|---|---|
| EP | 1128174 A2 | 8/2001 |
| EP | 1864784 A1 | 12/2007 |
| WO | 2008044349 A1 | 4/2008 |
| WO | 2010117382 A1 | 10/2010 |

OTHER PUBLICATIONS

Sari et al., "Applications of laser transmission processes for the joining of plastics, silicon and glass micro parts," Microsyst Technol (2008) 14: 1879-1886, published online Jul. 18, 2008.

Theppakuttai et al., "Localized Laser Transmission Bonding for Microsystem Fabrication and Packaging," Journal of Manufacturing Processes, vol. 6, No. 1, 2004 (8 pp).

(56) References Cited

OTHER PUBLICATIONS

Wild et al., "Locally selective bonding of silicon and glass with laser," Sensors and Actuators A: Physical, vol. 93, Issue 1, Aug. 25, 2001, p. 63-69.

Park, "Characterization of transmission laser bonding (TLB) technique for microsystem packaging," Arizona State University, May 2006 (135 pp.).

EnerChip CBC012, Rechargeable Solid State Energy Storage: 12µAh, 3.8V, Cymbet Corporation, DS-72-02 Rev A, 2009-2010 Cymbet™ Corporation (5 pp.).

Thinergy, The Leading Thin Power Solution, 2010 Infinite Power Solutions, Inc. (2 pp.), accessed online Oct. 14, 2010 at http://www.infinitepowersolutions.com/product/thinergy.

U.S. Appl. No. 12/912,433, by Ralph B. Danzl, filed Oct. 26, 2010.

U.S. Appl. No. 12/977,890, by David A. Ruben, filed Dec. 23, 2010.

Office Action from related U.S. Appl. No. 12/977,890 dated Dec. 31, 2012 (17 pages).

International Search Report and Written Opinion of PCT/US2011/033986, dated Feb. 10, 2012, 11 pp.

Gillner et al., "Laser Bonding of Micro Optical Components," Proceedings of SPIE, vol. 4941, pp. 112-120, Oct. 30, 2003.

Witte et al., "Laser joining of glass with silicon," Proceedings of SPIE, vol. 4637, Jan. 21, 2002, pp. 487-495.

Amendment from U.S. Appl. No. 12/912,433 filed Jun. 7, 2013 (13 pages).

Office Action from U.S. Appl. No. 12/977,890 dated Jun. 5, 2013 (19 pages).

Office Action from co-pending U.S. Appl. No. 12/912,433 dated Mar. 14, 2013 (14 pages).

Lau, "MEMS Structures for Stress Measurements for Thin Films Deposited Using CVD", Master of Science Thesis, Massachusetts Institute of Technology, Feb. 2001, 79 pages.

Lea et al., "DRIE from MEMS to wafer-level packaging", Solid State Technology, Dec. 2007; 50 (12) 8 pages. Retrieved online on Oct. 11, 2010. Available online at url:http://www.electroiq.com/ElectrolQ/en-us/index/display/ Eemiconductor_Article_Tools_Template.articles.solid-state-technology.volume-50.issue-12.features.mems.drie-from-mems-to-wafer-level-packaging.html.

Oberg et al., Machinery's Handbook, 25th edition, Industrial Press, New York, NY, 1996: title page, copyright page and p. 267, 2 pages.

Osterberg et al., "M-Test: A Test Chip for MEMS Using Electostatically Actuated Test Structures", Journal of Microelectromechanic Systems, Jun. 1997; 6(2): pp. 107-118.

Pham et al., "High-aspect-ratio bulk micromachined vias contacts," ProcSAFE and Prorisc 2004, Veldhoven, NL, Nov. 25-26, 2004, pp. 742-746.

Potkay, "Long Term, Implantable Blood Pressure Monitoring Systems", Biomed Microdevices, 2008; 10:379-392. Published online Dec. 20, 2007.

Brown, "Precision Laser Welding of Clear Thermoplastics Without Additives", Medical Design Technology, Aug. 5, 2013, 7 pages. Located on the World Wide Web at http://www.mdtmag.com/articles/2013/08/precision-laser-welding-clear-thermoplastics-without-additives.

Final Office Action from U.S. Appl. No. 12/912,433 dated Sep. 24, 2013, "Laser Assisted Direct Bonding", (17 pages).

Response to Office Action dated Sep. 24, 2013, from U.S. Appl. No. 12/912,433, filed Nov. 12, 2013, 14 pp.

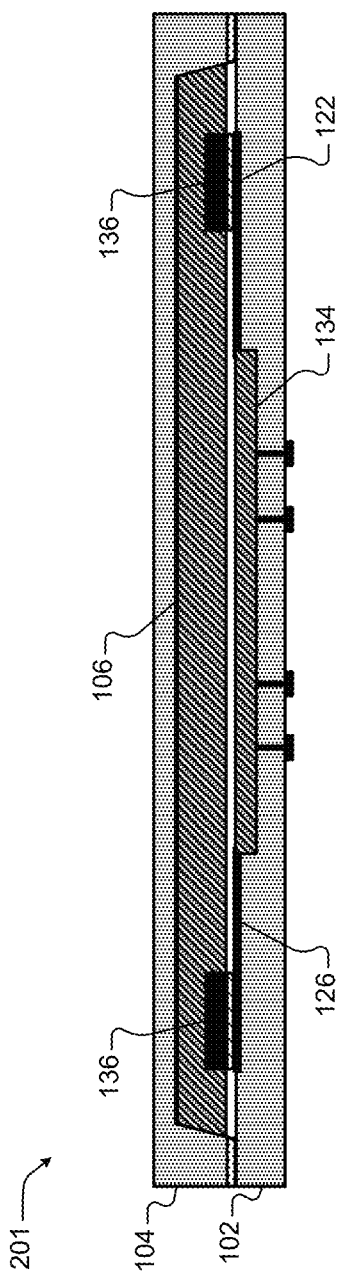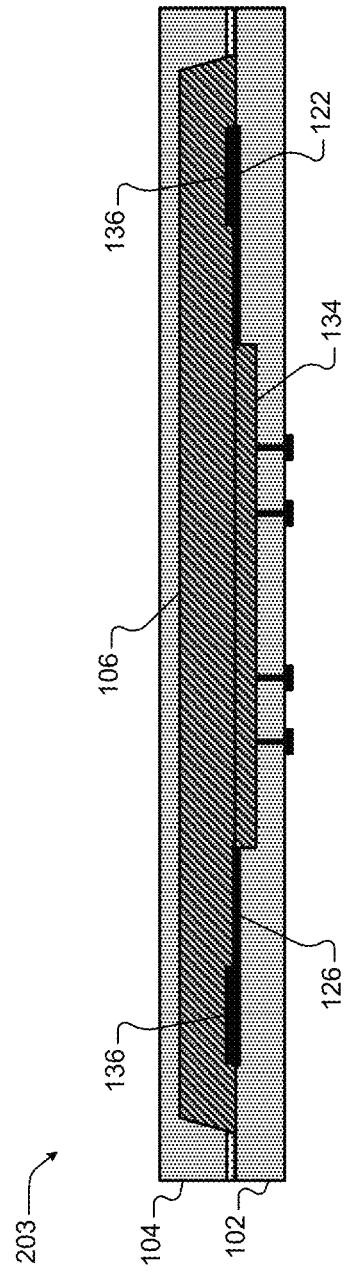

WAFER-SCALE PACKAGE INCLUDING POWER SOURCE

This application claims the benefit of U.S. Provisional Application No. 61/406,961, entitled, "WAFER-SCALE PACKAGE INCLUDING POWER SOURCE," and filed on Oct. 26, 2010, the entire content of which is incorporated herein by reference.

TECHNICAL FIELD

The disclosure relates to packages, and, more particularly, to wafer-scale packages including a power source and an electronic circuit.

BACKGROUND

The semiconductor and electronics industry uses material bonding techniques to bond different substrates together during semiconductor/circuit fabrication. Direct bonding is one type of bonding technique that is frequently used to bond different materials together. Direct bonding involves bonding different materials together without the aid of a specific bonding agent such as, for example, adhesive, wax, solder, or the like. Direct bonding techniques may be used to form component packages that house electrical components. A component package may be useful to protect the electrical components from different environmental conditions such as, e.g., pressure changes, moisture, bodily fluids, or the like.

In some examples, component packages may be placed in an oven after bringing the substrates of the component package in close contact to cause covalent bonds to form between the different substrates. Because this heating process included in forming a direct bond may involve heating the bond to an elevated temperature, temperature-sensitive components of the package may experience thermal damage when placed in a package that is subsequently sealed using direct bonding techniques. Moreover, because the process of forming a direct bond may involve one or more cycles of heating and cooling, mismatches between coefficients of thermal expansion for different substrates being bonded may cause warping and thermal stress fractures to develop between the different substrates. Warping and thermal stress fractures may weaken the bond between the different substrates and may reduce the hermeticity of a component package formed using direct bonding techniques.

SUMMARY

A packaged device according to the present disclosure may be configured for implantation in a patient or external attachment to a patient. The packaged device includes at least two substrates that are hermetically bonded together such that the two substrates define an enclosed cavity between the two substrates. A control module may be disposed within the enclosed cavity that is configured to determine a physiological parameter of the patient and/or to provide electrical stimulation to the patient. An energy storage device, such as a battery, may be included within the enclosed cavity and may provide power to the control module.

The packaged device may be fabricated at low temperature from a variety of materials. In some examples, the packaged device may include semiconductor and/or insulating substrates (e.g., silicon and/or glass). The substrates may be bonded using a laser assisted bonding technique that maintains a relatively low temperature within the packaged device during bonding so that the components in the packaged device may not be thermally damaged. Additionally, the packaged device produced using the low temperature bonding technique may not incur stress fractures that may adversely affect the hermeticity of the package.

In one example according to the present disclosure, a medical device comprises a first substrate, a second substrate, a control module, and an energy storage device. The first substrate includes at least one of a first semiconductor material and a first insulating material. The second substrate includes at least one of a second semiconductor material and a second insulating material. The second substrate is bonded to the first substrate such that the first and second substrates define an enclosed cavity between the first and second substrates. The control module is disposed within the enclosed cavity. The control module is configured to at least one of determine a physiological parameter of a patient and deliver electrical stimulation to the patient. The energy storage device is disposed within the cavity and is configured to supply power to the control module.

In another example according to the present disclosure, a device comprises a first substrate, a second substrate, and a battery. The first substrate includes at least one of a first semiconductor material and a first insulating material. The first substrate includes a plurality of bonding pads. The second substrate includes at least one of a second semiconductor material and a second insulating material. The second substrate is bonded to the first substrate such that the first and second substrates define an enclosed cavity between the first and second substrates. The battery is housed in the enclosed cavity. The battery includes conductive contacts disposed on a bottom surface of the battery. The conductive contacts are connected (e.g., soldered) to two or more of the plurality of bonding pads such that the bottom surface of the battery faces the surface of the first substrate that includes the bonding pads.

In another example according to the present disclosure, a method comprises connecting a control module to one of a first substrate and a second substrate. The first substrate includes at least one of a first semiconductor material and a first insulating material. The second substrate includes at least one of a second semiconductor material and a second insulating material. The control module is configured to one of determine a physiological parameter of a patient and deliver electrical therapy to the patient. The method further comprises connecting an energy storage device to one of the first and second substrates and interfacing the first and second substrates such that the first and second substrates define an enclosed cavity between the first and second substrates. The enclosed cavity includes the control module and the energy storage device. Additionally, the method comprises heating an interface between the first and second substrates to form a bond between the first and second substrates.

The details of one or more examples are set forth in the accompanying drawings and the description below. Other features, objects, and advantages will be apparent from the description and drawings, and from the claims.

BRIEF DESCRIPTION OF THE DRAWINGS

FIGS. 14A-14B show cross-sectional side views of example packaged devices including energy storage devices fabricated in a recessed region of a substrate.

DETAILED DESCRIPTION

Figure 1:
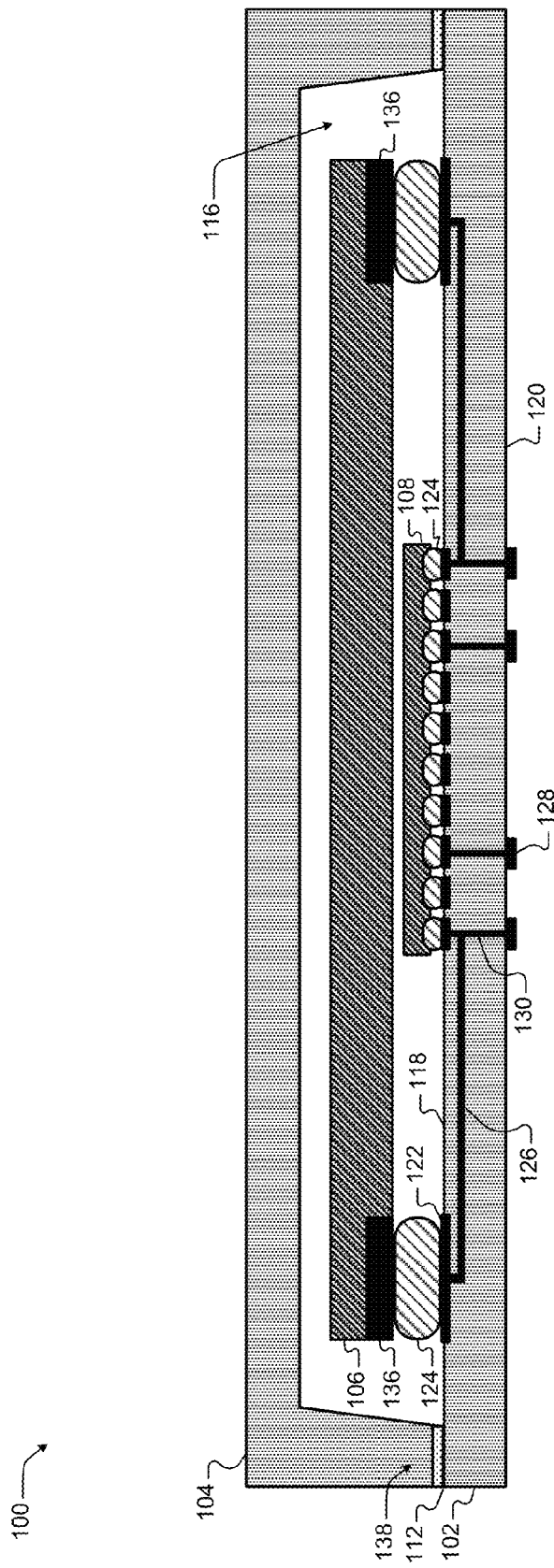
FIG. 1 shows a cross-sectional side view of a packaged device that includes a planar substrate, a recessed substrate, and various components.

As described herein, a hermetically sealed packaged device includes various electronic components housed within a package fabricated using two substrates. In general, fabrication of the packaged devices includes attaching the various components to one of the substrates, then attaching the two substrates together such that the various components are housed within a cavity defined by the two substrates.

A packaged device of the present disclosure may include a variety of different electrical components. In one example, the packaged device may include one or more integrated circuits. Integrated circuits may be fabricated on one or more integrated circuit dice (e.g., silicon or glass) that are subsequently mounted in the packaged device. Additionally, or alternatively, the packaged device may include integrated circuits fabricated directly onto one or both of the substrates, e.g., embedded within or deposited onto the substrates.

The packaged device of the present disclosure may also include an energy storage device. In some examples, the energy storage device may include a battery (e.g., a solid state battery) and/or a capacitor. In examples where the energy storage device includes a battery, the battery may be fabricated as a discrete component and subsequently mounted within the packaged device. In other examples, the battery may be fabricated directly onto one or both of the substrates comprising the packaged device. In examples where the energy storage device includes a capacitor, the capacitor may be fabricated as a discrete component and subsequently mounted within the package or may be fabricated directly onto one or both of the substrates.

In some examples the packaged device may include a charging component that charges the energy storage device. By charging the energy storage device, the useful lifetime of the packaged device may be extended and the volume of the packaged device may be reduced. For example, when the energy storage device includes a battery, the volume of the battery may be reduced when a charging component is included in the packaged device since the battery may not be required to store an initial energy for the lifetime of the device, but may instead be recharged during the lifetime of the packaged device. The charging component may include a piezoelectric device, betavoltaic device, or a photovoltaic device, for example.

The packaged device of the present disclosure may include sensing components. For example, the packaged device may include a motion sensor (e.g., an inertial sensor) such as an accelerometer (e.g., one or more axis), and/or a gyroscopic sensor. Additionally or alternatively, the packaged device may include optical sensors that include an optical emitter and receiver that determine properties of the environment in which the packaged device is present. Additionally, or alternatively, the packaged device may include electrochemical sensors that interact with body tissues to sense the environment in which the packaged device is present. The sensing components, e.g., accelerometer, gyroscopic sensor, electrochemical sensor, and/or optical transceiver, may be fabricated directly onto one of the substrates that form the packaged device and/or may be fabricated on one or more dice that are subsequently mounted in the packaged device.

In some examples, the packaged device may include components used for communication with devices external to the packaged device. For example, the packaged device may include an antenna. The antenna may be fabricated on a die (e.g., glass or semiconductor) that is mounted within the package. Alternatively, or additionally, the antenna may be fabricated on one of the substrates of the packaged device. Alternatively, or additionally, the antenna may be fabricated as a wirewound coil and mounted on one of the substrates within the package.

In some examples, the packaged device may include passive components, e.g., integrated or discrete passive components, such as resistors, capacitors, inductors, etc. Additionally, or alternatively, in some examples the packaged device may include micro-electro-mechanical system (MEMS) components such as beams or diaphragms.

The packaged device may also include conductive traces that interconnect components included in the packaged device and that interface these components to devices external to the packaged device. For example, the packaged device may include one or more layers of conductive traces that are deposited on or within one or both substrates.

The packaged device may include one or more package vias that extend from an inside of the packaged device, through one or both of the substrates, to an outside surface of the packaged device. In one example, the packaged device may be designed for implantation into a patient as an implantable medical device, and the components of the packaged device may sense physiological electrical signals through the package vias and/or provide electrical therapy to a patient through the one or more of the vias. In other examples, the components of the packaged device may communicate using an intrabody communication (e.g., tissue conductance communication) to other devices located on or within the patient through the package vias.

In some examples, the packaged device may be implanted in a patient or attached externally to a patient. When the packaged device is configured to be implanted in the body of a patient, the packaged device may include an exterior coating that enhances biocompatibility of the packaged device for implantation, e.g., provides a greater biocompatibility than the materials used as the substrate of the packaged device (e.g., glass or silicon). For example, the exterior coating may include a titanium coating that covers the outside of the packaged device, excluding any electrodes that are external to the packaged device. In another example, the exterior coating may include a silicone layer that covers the outside of the packaged device, excluding any electrodes that are external to the packaged device.

The packaged device may include a variety of features depending on which components are included in the packaged device. The components (e.g., integrated circuits) of the packaged device may measure physiological parameters of a patient. For example, the components may measure physiological parameters of the patient using the accelerometer, gyroscopic sensor and optical transceiver. Additionally, or alternatively, the components may measure physiological parameters of the patient based on electrical signals received through the package vias. Additionally, or alternatively, the components of the packaged device may provide electrical stimulation (e.g., cardiac pacing and/or neurostimulation) through the package vias.

In some examples, the packaged device may not include package vias that extend from the inside of the packaged device to the outside surface of the packaged device. In these examples, the packaged device may include a sensor (e.g., temperature, pressure, accelerometer, gyroscopic sensor, and/or optical transceiver) that measures physiological parameters and a communication component which may communicate the data outside of the packaged device. For example, when the sensor is a motion sensor such as an accelerometer or a gyroscopic sensor, the packaged device may include electronic components that receive signals from the motion sensor and determine an orientation of the patient and/or an activity level of the patient based on the received signals. The communication device (e.g., including an antenna) may then transmit the physiological parameters (e.g., the orientation as determined based on an orientation of implant) determined by the electronic circuit to devices outside of the packaged device.

In examples when the packaged device includes package vias, components within the packaged device may include additional features. For example, the components may measure electrical physiological parameters of the patient in which the device is implanted or to which the device is connected externally. Electrical physiological parameters may include external electrocardiogram signals (ECG), internal electrocardiogram signals (IEGM), electroencephalogram signals (EEG), or other electrogram signals (e.g., electromyogram signals, gastric signals, peripheral neurological signals). Additionally, or alternatively, the components of the packaged device may provide electrical therapy to the patient, e.g., the components may provide neurostimulation and/or cardiac pacing functions through the package vias. Furthermore, when the packaged device includes a communication component, such as an antenna, the components of the packaged device may transmit data indicating the physiological parameters sensed by the packaged device. Additionally, or alternatively, components of the packaged device may communicate the physiological data to devices external to the packaged device using tissue conductance communication.

FIG. 1 illustrates a cross-sectional side view of a packaged device 100 that includes a planar substrate 102, a recessed substrate 104, and various components such as an energy storage device (ESD) 106 and a die 108 (e.g., an integrated circuit die). Recessed substrate 104 defines a recessed region, e.g., illustrated at 110 in FIG. 3D. Package components, e.g., ESD 106 and die 108, are attached to and supported by planar substrate 102. Recessed substrate 104 may be connected to planar substrate 102 at an interface 112 formed between planar substrate 102 and recessed substrate 104. Depending on the materials used for planar and recessed substrates 102, 104 and the method used to bond planar and recessed substrates 102, 104, interface 112 may include an interface material, such as a layer of amorphous silicon or a layer of metal (e.g., platinum). This interface material may be on the order of angstroms to microns thick depending on the material and bonding method used. In other examples, interface 112 may not include a layer of material deposited on either planar substrate 102 or recessed substrate 104, as illustrated at 112 in FIG. 8. A method of forming the bond between planar and recessed substrates 102, 104 is described further with reference to FIG. 7.

Figure 4:
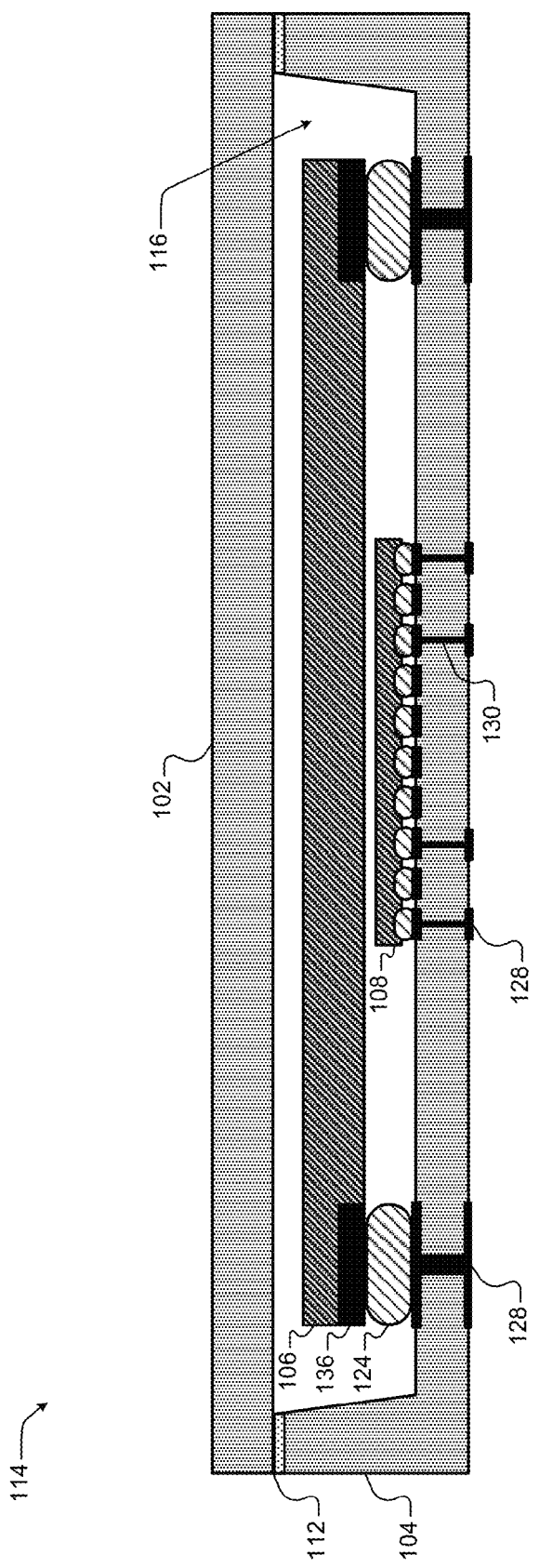
FIG. 4 shows a cross-sectional side view of an alternative packaged device.

Although packaged device 100 of FIG. 1 illustrates package components attached to planar substrate 102, in other examples, package components may be attached to recessed substrate 104 as illustrated by the cross-sectional side view of packaged device 114 of FIG. 4. Although packaged devices (e.g., packaged devices 100, 114) are illustrated in this disclosure as including planar substrate 102 and recessed substrate 104, a packaged device may include substrates having different geometries so long as various components may be housed within a cavity formed between the separate substrates. For example, both substrates included in a packaged device may each define recessed portions that enclose components of the packaged device.

Although packaged devices (e.g., packaged device 100, 114) of the present disclosure are illustrated as including a single cavity formed between two substrates, packaged devices of the present disclosure may include multiple cavities formed between multiple substrates bonded to a single supporting substrate. For example, a packaged device may include a single supporting substrate (e.g., planar substrate 102) and two capping substrates (e.g., recessed substrates 104) that are bonded together to form two separate cavities. In this example, a first cavity may be formed between the supporting substrate and a first capping substrate and a second cavity may be formed between the supporting substrate and a second capping substrate. The electrical components of the packaged device including two cavities may be included within the two separate cavities.

In some examples, packaged devices may be fabricated using a spacing substrate in order to increase a volume of the cavity of the packaged device. In these examples, components of a packaged device may be included on a supporting substrate, then a spacing substrate may be connected (e.g., around a perimeter of the components) to the supporting substrate. The spacing substrate may, for example, define a window that is configured to surround the components of the packaged device. Subsequently, a capping substrate may be placed over and connected to the spacing substrate such that the supporting substrate, spacing substrate, and capping substrate define a cavity in which the components are housed.

Planar substrate 102 and recessed substrate 104 may include a variety of materials. For example, planar and recessed substrates 102, 104 may include, but are not limited to, semiconductor materials and insulating materials. In some cases, planar substrate 102 and/or recessed substrate 104 may include silicon substrates and/or silicon carbide substrates. Planar substrate 102 and/or recessed substrate 104 may include glass substrates, such as borosilicate glass, sapphire, or fused silica. Although substrates 102, 104 of the present disclosure are described as including semiconductor and insulating materials, it is contemplated that other materials may be used as substrates 102, 104 of the present disclosure.

Planar substrate 102 and recessed substrate 104 of the packaged devices (e.g., 100, 114) may be fabricated from the same materials, or may be fabricated from different materials. In one example, planar and recessed substrates 102, 104 may both comprise glass substrates, e.g., be cut from a glass wafer (e.g., borosilicate glass). In this example, a plurality of packaged devices may be fabricated on a single glass wafer, then subsequently cut from the glass wafer to form individual packaged devices as illustrated in FIG. 1. In another example, both planar and recessed substrates 102, 104 may comprise a semiconductor material, e.g., both substrates 102, 104 may be cut from silicon wafers. In this example, a plurality of packaged devices may be fabricated on a single silicon wafer, then subsequently cut from the silicon wafer to form individual packaged devices as illustrated in FIG. 1. In another example, one of substrates 102, 104 may include a glass substrate and the other of substrates 102, 104 may comprise another material, such as a semiconductor substrate (e.g., a silicon slab cut from a silicon wafer). In this example, a plurality of packaged devices may be fabricated on either a glass wafer or a wafer of another material, then subsequently cut from the wafer to form individual packaged devices as illustrated in FIG. 1.

The formation of the bond, illustrated as interface 112, between planar and recessed substrates 102, 104 may depend on the combination of materials from which planar and recessed substrates 102, 104 are selected. For example, two glass substrates may be bonded together when an interface layer (e.g., amorphous silicon) is added to one of the substrates 102, 104. In another example, two silicon substrates may be bonded together without an added interface layer. Example details regarding a method of bonding planar and recessed substrates 102, 104 are included in greater detail with respect to FIG. 7.

Planar substrate 102 and recessed substrate 104 are bonded together such that planar substrate 102 and recessed substrate 104 define a cavity 116 within packaged device 100. Planar substrate 102 includes a surface 118 that defines a portion of cavity 116. Surface 118 may be referred to as interior surface 118 of planar substrate 102. A surface 120 of planar substrate 102 that is on an opposite side of interior surface 118 may form a portion of the outside surface of packaged device 100. Surface 120 may be referred to as an exterior surface 120 of planar substrate 102.

In some examples, packaged device 100 may be on the order of 0.75 millimeters to 3 millimeters thick, depending on the overall thickness of planar substrate 102, recessed substrate 104, and components included within cavity 116. For example, planar substrate 102 may have a thickness of approximately 200 micrometers or less, die 108 may have a thickness within a range of 100-150 micrometers or less, and ESD 106 may have a thickness on the order of 200 micrometers or greater. An area of packaged device 100 (e.g., a surface area of planar substrate 102) may be on the order of 10 to 50 mm$^2$ resulting from widths in the range of 2 to 5 millimeters by lengths of 5 to 10 millimeters. Other example packaged devices according to the present disclosure may have dimensions that are greater or less than those described above. For example, a thickness of the packaged devices may be less than 0.75 millimeters or greater than 3 millimeters in some examples. Furthermore, a width and length of the packaged devices may be less than 2 millimeters or may be greater than 10 millimeters in some examples.

Planar substrate 102 may include bonding pads 122 on interior surface 118. Bonding pads 122 may include conductive material, e.g., metals, such as copper, aluminum, titanium, platinum, gold, and nickel. Components, such as ESD 106 and die 108, may be connected to bonding pads 122 using a solder material such as gold-tin or tin-lead. Individually deposited portions of solder material that form connections between components of packaged devices may be referred to as solder bumps 124. Bonding pads 122 may be electrically interconnected by conductive traces. For example, the conductive traces may be deposited as one or more layers on interior surface 118, or may be embedded (e.g. etched and deposited) in planar substrate 102. Example conductive traces that connect ESD 106 to die 108 are illustrated at 126. Conductive traces may include conductive material, e.g., metals, such as copper, aluminum, titanium, platinum, gold, nickel, or any other conductor suitable for electrically connecting components of packaged devices according to the present disclosure.

Although components may be attached to bonding pads 122 on interior surface 118 using solder bumps 124, components may be attached to bonding pads 122 using other methods. For example, components may be attached to bonding pads 122 using at least one of thermocompression stud bumping, conductive adhesives, anisotropically conductive films, tape automated bonding, and wire bonding.

In some examples, planar substrate 102 may include one or more external pads 128 deposited on exterior surface 120 of planar substrate 102. External pads 128 on exterior surface 120 may include conductive materials, e.g., metals, such as titanium, platinum, gold, niobium, or alloys of these materials. In some examples, when packaged device 100 is configured to be implanted in a patient, external pads 128 may include a biocompatible material such as titanium, platinum, gold, niobium, or alloys of these materials. Additionally, or alternatively, external pads 128 may include tantalum and/or alloys of tantalum.

In examples where planar substrate 102 includes external pads 128 on exterior surface 120 of planar substrate 102, planar substrate 102 may include package vias 130 that electrically connect bonding pads 122 and/or conductive traces on interior surface 118 to external pads 128 on exterior surface 120. In examples where planar substrate 102 includes a silicon substrate, package vias 130 may be formed using a through-silicon via formation process. In examples where planar substrate 102 includes glass (e.g., borosilicate float glass), package vias 130 may be formed using any conductive metal such as titanium, tungsten, copper, nickel, gold, platinum, and solders such as PbSn, AuSn, etc.

External pads 128 may generally be deposited along external surface 120 such that external pads 128 are nearly flush with external surface 120, e.g., external pads may be on the order of micrometers in thickness. In some examples, external pads 128 may receive electrical physiological signals such as ECG, IEGM, and EEG. Additionally, or alternatively, external pads 128 may provide electrical stimulation to a patient, such as cardiac pacing stimulation and/or neurostimulation. External pads 128 may also enable tissue conductance communication between components of packaged device 100 and devices external to packaged device 100. In some examples, package vias 130 may not terminate as external pads 128, but instead may be connected to leads 132-1, 132-2 as described herein with respect to FIG. 12.

Various components may be included in packaged devices (e.g., packaged devices 100, 114) according to the present disclosure. For example, components may include analog/digital integrated circuits that provide signal conditioning functions (e.g., filtering and amplification), signal processing functions, logic functions. Integrated circuits may also include memory (e.g., volatile/non-volatile) that stores programs used by the integrated circuits to provide the functions associated with the integrated circuits described herein. Integrated circuits may also store measured physiological parameters in memory.

Integrated circuits included in packaged devices may be fabricated on one or more dice (e.g., die 108 of FIG. 1) included in packaged devices. In another example, integrated devices (e.g., integrated circuits) may be fabricated on or within planar substrate 102 (e.g., integrated device 134 of FIG. 11C) when planar substrate 102 includes a semiconductor material (e.g., silicon).

In some examples, integrated circuits in packaged device 100 may monitor physiological parameters of a patient in which packaged device 100 is implanted, or to which packaged device 100 is attached. In some examples, integrated circuits in packaged device 100 may be configured to measure electrical physiological signals, such as ECG, IEGM, and EEG through package vias 130 using external pads 128 and/or leads 132-1, 132-2 that extend into the body of the patient.

In other examples, integrated circuits in packaged device 100 may be configured to determine impedance between external pads 128 and/or leads 132-1, 132-2 attached to packaged device 100. In one example, integrated circuits may measure impedance by applying a voltage between two of the external pads (or leads) and subsequently measuring a current generated in response to the applied voltage. The integrated circuit may then measure impedance to determine lead integrity. In another example, the integrated circuit may be used to measure nerve response with the device connected to a nerve cuff.

In other examples, integrated circuits in packaged device 100 may be configured to provide electrical therapy to the patient. For example, the integrated circuits may perform cardiac pacing and/or neurostimulation functions, depending on the application for which packaged device 100 is implanted.

Integrated circuits, and other components (e.g., sensors) included in packaged device 100 may receive power from ESD 106 included. Using the power provided by ESD 106, integrated circuits included in packaged device 100 may provide amplification functions, filtering functions, logic functions, and signal processing functions. In some examples, integrated circuits may provide electrical stimulation (e.g., cardiac pacing and/or neurostimulation) to the patient using power received from ESD 106. In other examples, integrated circuits may monitor electrical physiological signals of the patient using power received from ESD 106.

ESD 106 may include any suitable device that stores energy and that may be disposed within cavity 116. In one example, ESD 106 may include a battery, such as a solid state battery. In some examples, when ESD 106 includes a solid state battery, the solid state battery may include lithium phosphorous oxynitride (LiPON). Although a solid state battery may be used, in other examples, ESD 106 may include other types of battery structures and chemistries. For example, ESD 106 may include a thin film battery structure. In some examples, when ESD 106 includes a solid state battery, the solid state battery may not comprise a typical thin film structure. In some examples, ESD 106 may include a rechargeable battery. In other examples, ESD 106 may include a non-rechargeable battery.

ESD 106 may include ESD contacts 136 that provide a connection point for ESD 106 to other components of packaged device 100. When ESD 106 includes a solid state battery, ESD contacts 136 may be conductive contacts arranged along the bottom surface of the battery. The conductive contacts arranged on the solid state battery may be contacted using solder bumps 124, for example. Accordingly, when a solid state battery is included in packaged device 100 as ESD 106, the solid state battery may be configured to be connected to bonding pads 122 using solder bumps 124. The size of solder bumps 124 used to connect devices to planar substrate 102 may vary, as illustrated in FIG. 1. For example, solder bumps 124 used to connect ESD 106 to planar substrate 102 may be relatively larger than solder bumps 124 used to connect die 108 to planar substrate 102 since die 108 is arranged closer to planar substrate 102 between ESD 106 and planar substrate 102 as shown in FIG. 1.

In some examples, ESD 106 may include a capacitor that stores charge for subsequent transfer to components of packaged device 100. When ESD 106 includes a capacitor, the capacitor may include contacts on a surface of the capacitor that may be connected to bonding pads 122 of planar substrate 102 using solder bumps 124.

In some examples, packaged device 100 may include a charging device that charges ESD 106 and therefore may prolong the lifetime of packaged device 100. The charging device may include a betavoltaic or photovoltaic device that generates electrical current that is received by ESD 106. The charging device may include a photovoltaic device in examples where packaged device 100 is externally fixed to the patient. In this case, one or both of planar and recessed substrates 102, 104 may be transparent to incident light (e.g., a borosilicate glass). In other examples, the charging device may include a piezoelectric generator, a radioisotope thermoelectric generator, a thermoelectric Peltier generator, or an inductive charging device (e.g., including an inductive coil).

The charging device may be included on a die that is mounted within package 100, such as die 108. In other examples, the charging device may be fabricated onto interior surface 118 of planar substrate 102, e.g., as an integrated device similar to integrated device 134 of FIG. 11C.

In some examples, packaged device 100 may include sensors such as an accelerometer or a gyroscopic sensor. Sensors included in packaged device 100 may receive power from ESD 106. Sensors, e.g., accelerometers and gyroscopic sensors, may be included in packaged devices as one or more dice (e.g., on die 108). Sensors may also be integrated onto one or both of planar and recessed substrates 102, 104 of packaged devices, e.g., as an integrated device similar to integrated device 134 of FIG. 11C. In examples where sensors include an optical transceiver component that emits light and receives reflected portions of the emitted light, the optical transceiver component may be included on one or more dice or integrated into one or both of planar and recessed substrates 102, 104.

Integrated circuits in packaged device 100 may be configured to determine various physiological parameters of the patient based on data received from the sensors. For example, integrated circuits may determine an orientation of the patient, and an activity level of the patient based on data received from motion sensors (e.g., accelerometer and gyroscopic sensors) included in the packaged device 100. In other examples, the integrated circuits may determine changes in metabolite levels in the blood, such as oxygen saturation levels or glucose levels, or changes in tissue perfusion based on data received from the optical transceiver component, when included in packaged device 100.

In some examples, packaged device 100 may include communication devices, such as antennas. When packaged device 100 includes an antenna, the antenna may be included on one or more dice mounted in packaged device 100 and/or on one or both of planar and recessed substrates 102, 104. In some examples, an antenna within packaged device 100 may communicate using telemetry protocols established by the medical industry. Integrated circuits included within packaged device 100 may transmit and receive data via the antenna included in packaged device 100. Data may include physiological parameters of the patient measured by sensors and physiological electrical signals measured through package vias 130.

Additionally, or alternatively, packaged device 100 may include a tissue conductance communication component (i.e., an interbody communication component) that communicates with devices external to packaged device 100 using tissue conductance communication. During tissue conductance communication, packaged device 100 may apply or receive voltage signals at external pads 128 or via leads 132 to communicate with external devices.

Figure 2:
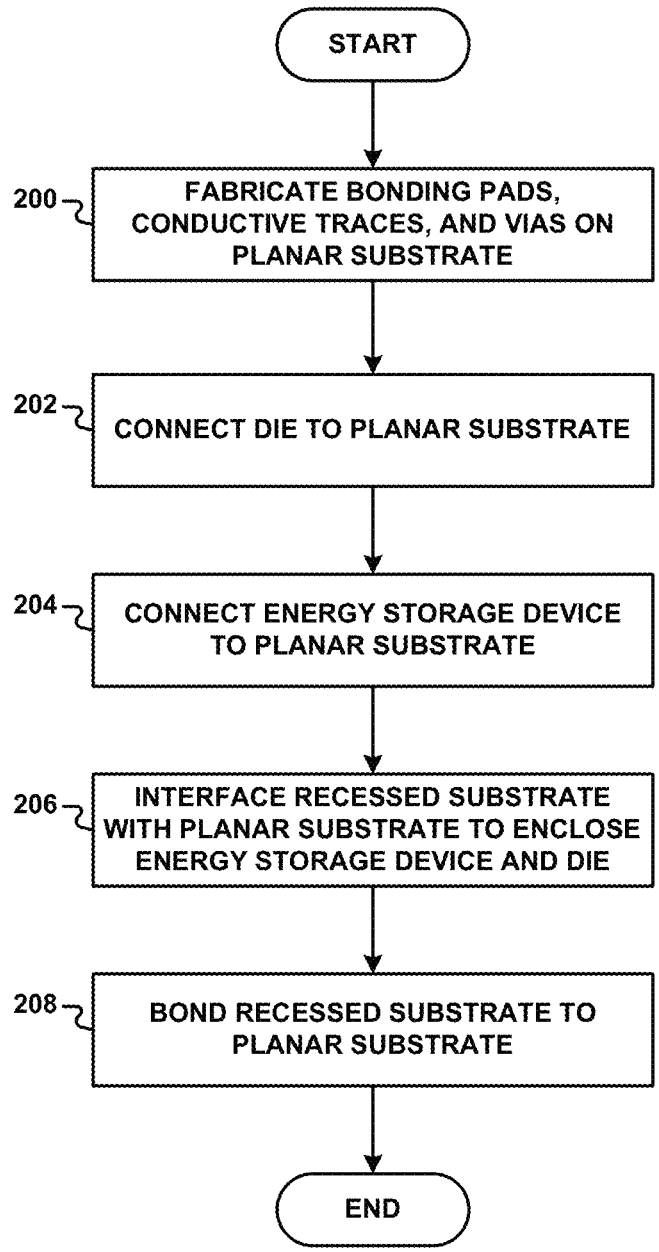
FIG. 2 shows an example flowchart of a method for fabricating the packaged device of FIG. 1.

FIG. 2 shows an example flowchart of a method for fabricating packaged device 100. FIGS. 3A-3D illustrate cross-sectional side views of construction of packaged device 100. As disclosed herein, the techniques used for fabricating packaged device 100 may be generally applicable for fabricating other packaged device structures according to the present disclosure. Although FIGS. 3A-3D illustrate construction of a single packaged device 100, a plurality of packaged devices 100 may be fabricated on a single substrate (e.g., a silicon or glass wafer) and then subsequently cut from the single wafer after construction of the plurality of packaged devices 100. In other words, substrate 102 may represent a portion of a larger substrate (e.g., a wafer) on which packaged device 100 is fabricated. In some examples, substrate 104 may also represent a portion of a larger substrate that includes a plurality of recessed regions 110 that is placed over top of a single wafer to form a plurality of packaged devices 100.

Figure 3A:
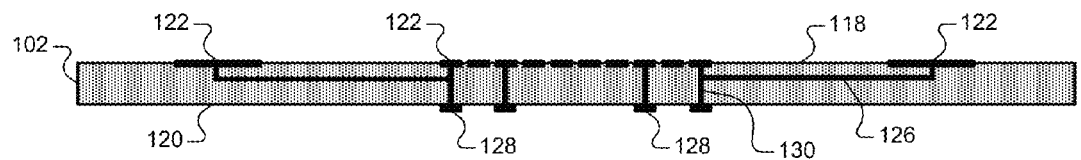
FIGS. 3A-3D illustrate cross-sectional side views of construction of the packaged device of FIG. 1.

Bonding pads 122, conductive traces, and package vias 130 may be fabricated on a planar substrate 102 (200) as illustrated in FIG. 3A. For example, bonding pads 122, conductive traces, and package vias 130 may be fabricated using a series of masking, etching, and deposition steps. Bonding pads 122 may be electrically interconnected by the conductive traces which may be deposited on interior surface 118 and/or embedded within planar substrate 102. Bonding pads 122, conductive traces, and package vias 130 may include a variety of conductive materials. Bonding pads 122 on interior surface 118 may be used for subsequent mounting of ESD 106 or other dice that may include various integrated circuits and sensors, for example. In example packaged devices that may include energy storage devices, integrated circuits, and/or sensors fabricated on interior surface 118, such devices may be fabricated before the following operations in which components are mounted to interior surface 118.

Figure 3B:
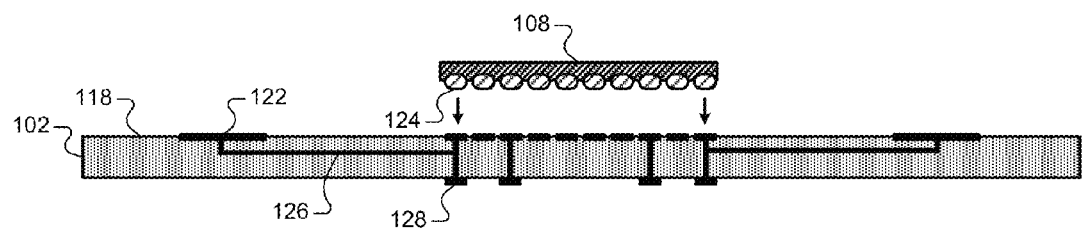

Die 108 may then be connected to bonding pads 122 on interior surface 118 of planar substrate 102 (202) as illustrated in FIG. 3B. Solder material, e.g., gold-tin or tin-lead, may be added to bonding pads located on a bottom surface of die 108 prior to mounting die 108 on planar substrate 102. Solder material added to bonding pads of die 108 may form solder bumps 124 on the bonding pads of die 108. During mounting, die 108 may be placed on bonding pads 122, and solder bumps 124 may be melted and subsequently cooled to providing electrical and physical connection of die 108 to bonding pads 122.

Figure 3C:
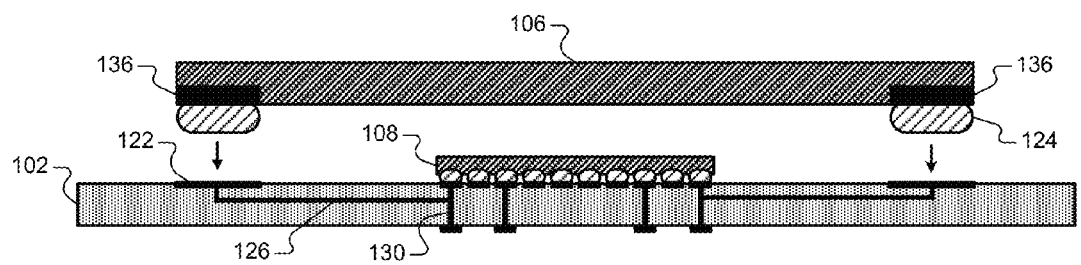

ESD 106 (i.e., ESD contacts 136) may then be connected to bonding pads 122 on interior surface 118 of planar substrate 102 (204) as illustrated in FIG. 3C. ESD contacts 136 of ESD 106 may be included on a bottom surface of ESD 106, e.g., the surface of ESD 106 facing interior surface 118 of planar substrate 102. ESD contacts 136 may be configured to be bonded to bonding pads 122 using solder bumps 124. Solder material may be added to ESD contacts 136 prior to mounting ESD 106 on planar substrate 102. In some examples, ESD 106 may be placed over top of die 108 and connected to bonding pads 122 that are arranged outside the periphery of die 108. In other words, ESD 106 may be mounted on planar substrate 102 such that ESD 106 straddles die 108. Thus, after connection of ESD 106, die 108 may be sandwiched between ESD 106 and planar substrate 102.

Figure 3D:
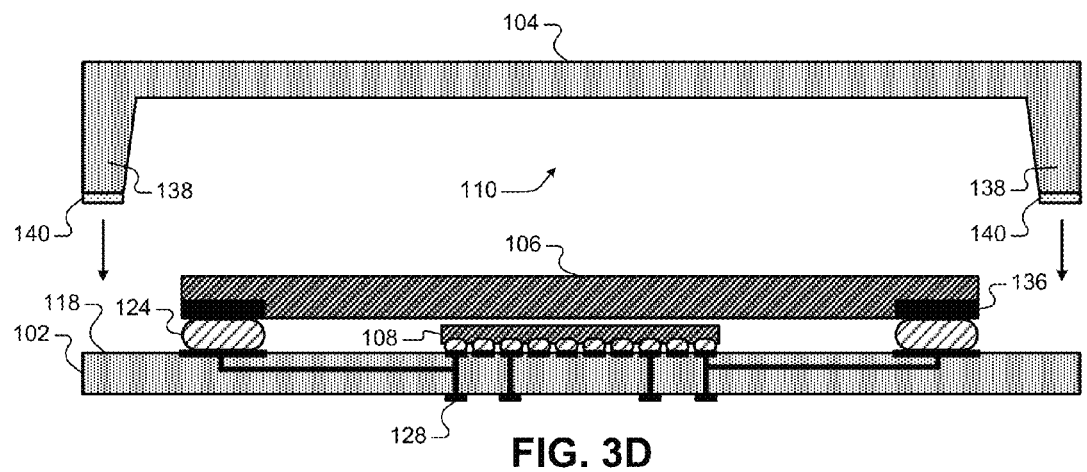
Figure 9:
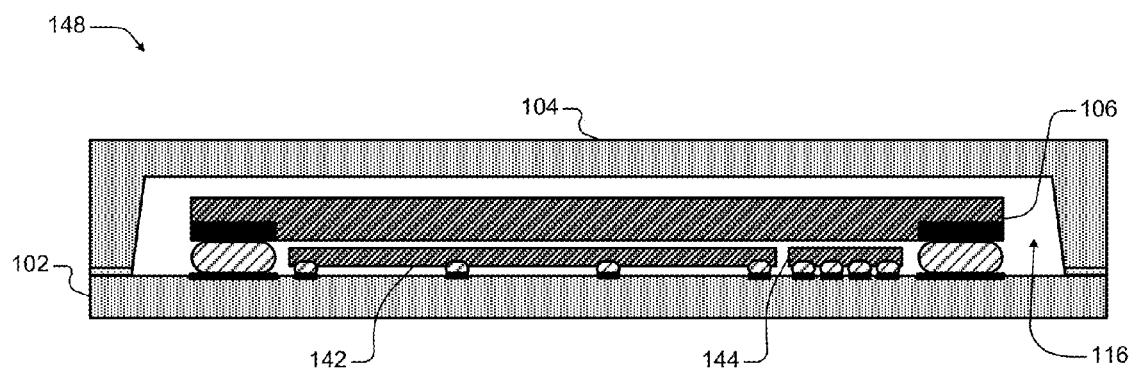
FIG. 9 shows a cross-sectional side view of a packaged device that includes more than one die mounted under an energy storage device.
Figure 10A:
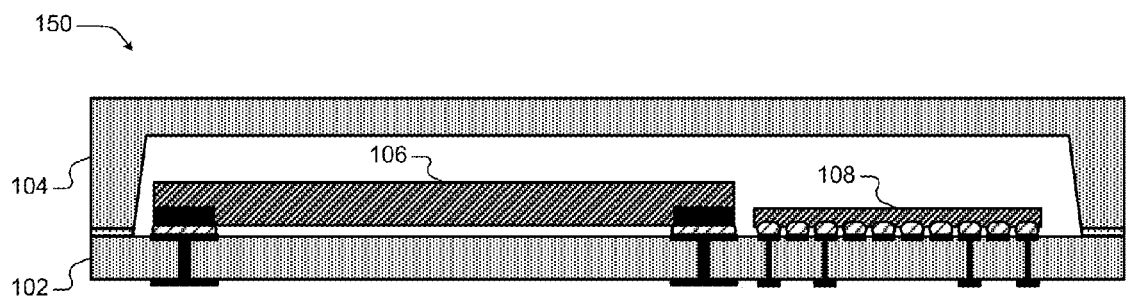
FIGS. 10A-10C show cross-sectional side views of example packaged devices including various arrangements of adjacent devices.
Figure 10B:
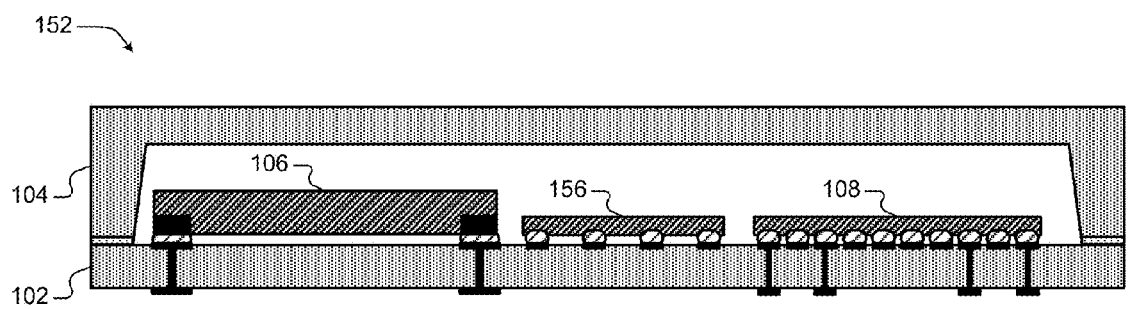
Figure 10C:
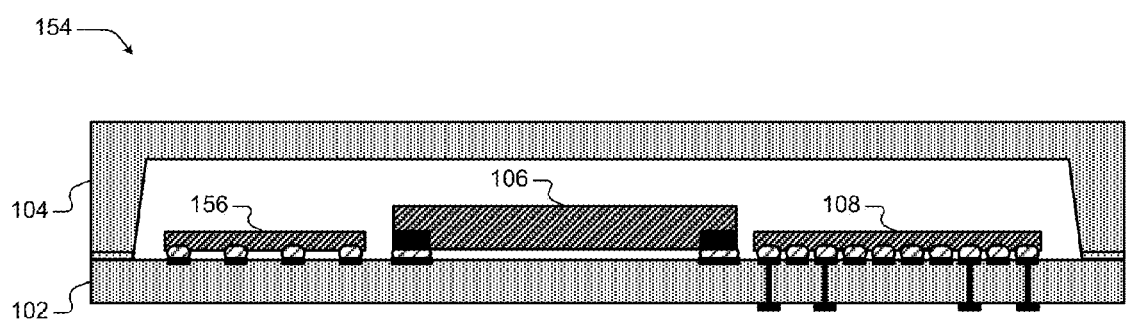

Although ESD 106 is illustrated as straddling a single die 108 in FIG. 1 and FIG. 3D, in other examples, ESD 106 may straddle more than a single die. For example, ESD 106 may straddle two or more dice as illustrated in FIG. 9. Additionally, or alternatively, ESD 106 may straddle integrated circuits or other devices integrated into planar substrate 102, as illustrated in FIG. 11C. In some examples, ESD 106 may not straddle a die, but may be connected to bonding pads 122 on interior surface 118 beside dice, as illustrated in FIG. 10A-10C.

Recessed substrate 104 can be then placed over top of ESD 106 and die 108 so that recessed substrate 104 is in contact with planar substrate 102 (206) as illustrated in FIG. 3D. Recessed substrate 104 includes a rim 138 that circumscribes recessed region 110. Rim 138 may include a flattened surface area that circumscribes recessed region 110. Recessed substrate 104 interfaces with planar substrate 102 at the flattened surface of rim 138. Recessed substrate 104 may be bonded to planar substrate 102 at the interface between the flattened surface of rim 138 and planar substrate 102 (208). For example, recessed substrate 104 and planar substrate 102 may be direct bonded at the interface between the flattened surface of rim 138 and planar substrate 102, then subsequently exposed to a heating source (e.g., a laser or other light source) in order to enhance the strength of the direct bond.

Figure 7:
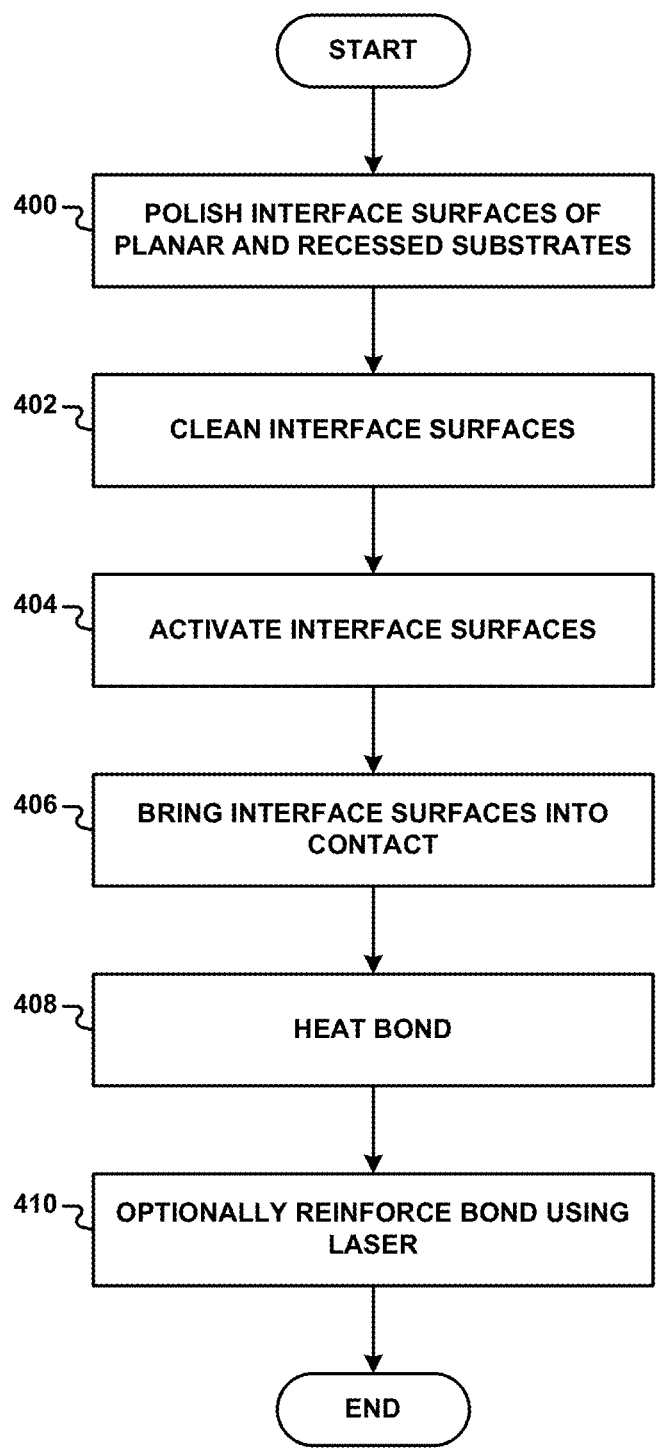
FIG. 7 shows an example flowchart of a method for bonding two substrates.

An example method used to bond planar and recessed substrates 102, 104 is described in detail with respect to FIG. 7. In some examples, as illustrated in FIG. 3D, an interface layer 140 may be deposited on rim 138 prior to placing recessed substrate 104 in contact with planar substrate 102. For example, when planar and recessed substrates 102, 104 include glass substrates, interface layer 140 (e.g., amorphous silicon) may be deposited on rim 138 using a sputtering process. In this example, interface layer 140 may promote bonding between recessed and planar substrates 102, 104 by forming a light absorbing layer (e.g., when a laser is used to promote bonding) or by forming a conductive layer (e.g., to facilitate an anodic bond). In other examples, where one or both of substrates 102, 104 include silicon substrates, planar and recessed substrates 102, 104 may be bonded without deposition of interface layer 140. In still other examples, in addition to, or in lieu of bonding as described with respect to FIG. 7, substrates 102, 104 may be adhered together and/or sealed, e.g., using benzocyclobutene (BCB) or a liquid crystal polymer (LCP). In other examples, a bonding process other than that described in FIG. 7 may be used, e.g., other semiconductor or MEMS bonding techniques.

Although the method illustrated and described with respect to FIG. 2 and FIGS. 3A-3D includes fabrication of bonding pads 122, conductive traces 126, and package vias 130 on planar substrate 102 along with connection of die 108 and ESD 106 to planar substrate 102, in some examples, recessed substrate 104 may include such components. For example, as illustrated in FIG. 4, recessed substrate 104 may include bonding pads 122, conductive traces 126, package vias 130, die 108, and ESD 106. Planar substrate 102 may be bonded to recessed substrate 104 to enclose the components included on recessed substrate 104.

Figure 5:
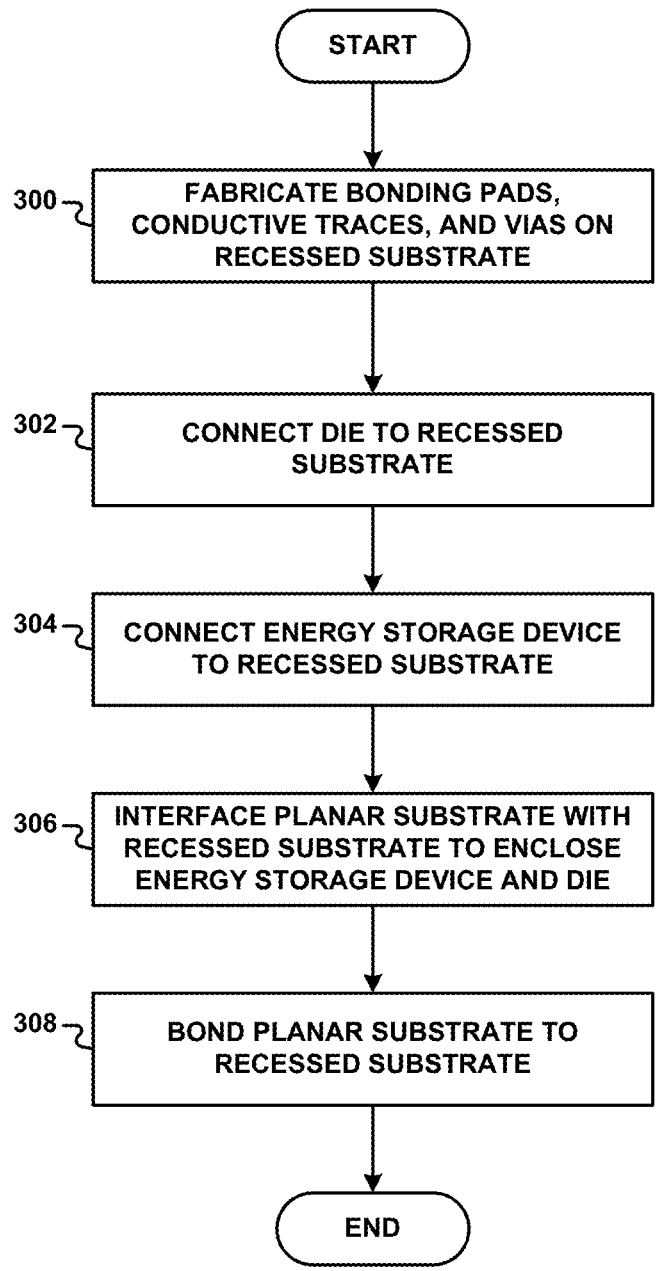
FIG. 5. shows an example flowchart of a method for fabricating the alternative packaged device of FIG. 4.
Figure 6A:
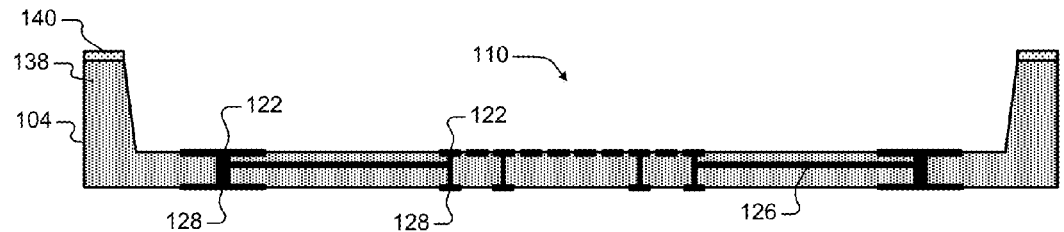
FIGS. 6A-6D illustrate cross-sectional side views of construction of the alternative packaged device of FIG. 4.
Figure 6B:
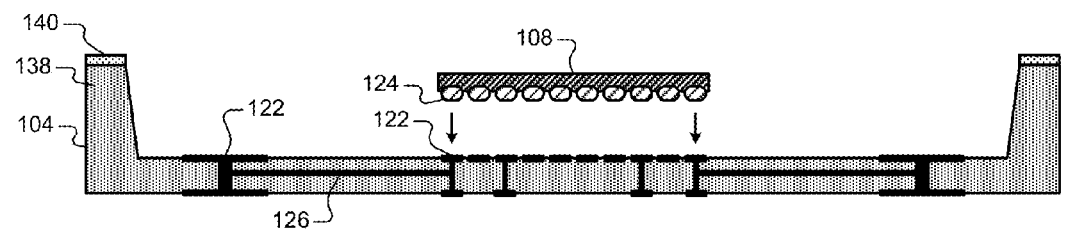
Figure 6C:
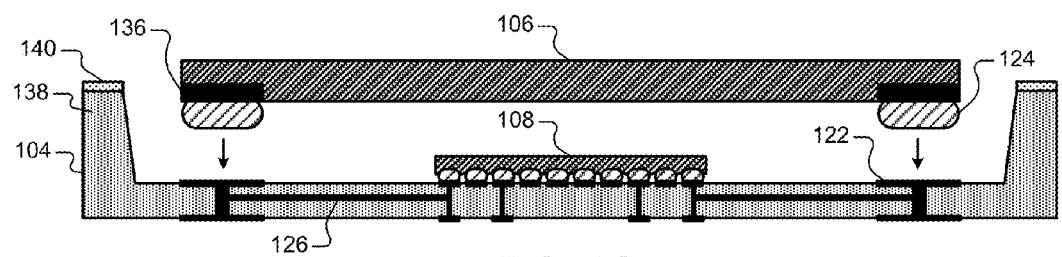
Figure 6D:
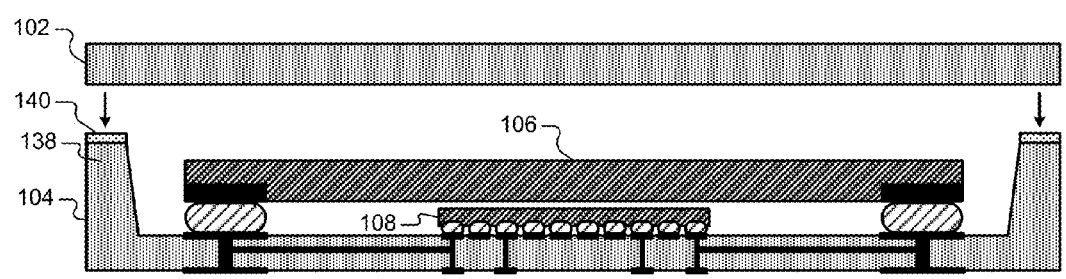

FIG. 5 shows an example flowchart of a method for fabricating packaged device 114 of FIG. 4. FIGS. 6A-6D illustrate cross-sectional side views of construction of packaged device 114. Bonding pads 122, conductive traces 126, and package vias 130 may be fabricated on recessed substrate 104 (300) as illustrated in FIG. 6A. In some examples, as described above, interface layer 140 (e.g., amorphous silicon) may also be deposited on the surface of rim 138 of recessed substrate 104. Die 108 may then be connected to bonding pads 122 on recessed substrate 104 (302) as illustrated in FIG. 6B. Solder material may be added to bonding pads located on a bottom surface of die 108 prior to mounting die 108 on recessed substrate 104. ESD 106 (i.e., ESD contacts 136) may then be connected to bonding pads 122 on recessed substrate 104 (304) as illustrated in FIG. 6C. Planar substrate 102 is then placed on recessed substrate 104, over top of ESD 106 and die 108, so that planar substrate 102 is in contact with recessed substrate 104 at the surface of rim 138 of recessed substrate 104 (306) as illustrated in FIG. 6D. Planar substrate 102 may then be bonded to recessed substrate 104 at the interface between the flattened surface of rim 138 and planar substrate 102 (308). The bonding may be performed using processes that are maintained at a low enough temperature to be compatible with ESD 106 and/or other devices (e.g., charge accumulators) within cavity 116. For example, recessed substrate 104 and planar substrate 102 may be direct bonded at the interface between the flattened surface of rim 138 and planar substrate 102, then subsequently treated with a laser that heats the interface in order to enhance the strength of the direct bond. An example method used to bond planar and recessed substrates 102, 104 is described in detail with respect to FIG. 7.

Although FIGS. 6A-6D illustrate construction of a single packaged device 114, a plurality of packaged devices 114 may be fabricated on a single substrate (e.g., a silicon or glass wafer) and then subsequently cut from the single wafer after construction of the plurality of packaged devices 114. In other words, substrate 104 may represent a portion of a larger substrate (e.g., a wafer) including a plurality of recessed regions 110 in which components of packaged device 114 are included. In some examples, substrate 102 may also represent a portion of a larger substrate that is placed over top of the single wafer including a plurality of recessed regions 110 to form a plurality of packaged devices 114.

FIG. 7 shows an example flowchart of a method for bonding planar substrate 102 to recessed substrate 104 such that a hermetic seal is formed between planar and recessed substrates 102, 104. Example methods for bonding two substrates are described in U.S. patent application Ser. No. 12/912,433, filed on Oct. 26, 2010 and entitled "Laser Assisted Direct Bonding", which is incorporated herein by reference in its entirety.

The process of bonding (e.g., directly bonding) two or more substrates together to form a unified structure may include first preparing the contact surfaces of the substrates and then placing the substrates in contact with one another to establish a bond (e.g., direct bond) between the substrates (e.g., without an adhesive layer). Subsequently, the bond may be heated in order to strengthen the bond. In one example, a laser may be directed at the interface between the substrates in order to heat the interface and to strengthen the bond. Using a laser to heat the interface may provide a localized energy (e.g., localized in the region of the interface) that sufficiently heats the interface to promote bonding, but does not substantially heat the substrates, the cavity, and the components connected to the substrates. For example, when using a laser to heat the interface, the packaged device may be heated to no greater than 200° C. In some examples, using the laser to heat the interface may not result in a welding (e.g., melting and coalescing) of materials at the interface.

Potential thermal damage to components of packaged device 100 may depend on a temperature to which the components are heated and a length of time for which the components are heated. In some examples, when ESD 106 includes a solid state battery including LiPON, the solid state battery may be damaged if kept at approximately 180° C. or greater for an extended period of time (e.g., greater than a few minutes), but may not be damaged at solder reflow conditions such as when using SnPb at 220° C. for two minutes or less.

Therefore, when using a laser to heat the interface, the components (e.g., a solid state battery) connected to the substrates may not be heated to a temperature that may damage the components. This may be in contrast to a scenario where the bond is heated using other methods, such as anodic, fusion, or glass frit bonding. These processes (e.g., anodic, fusion, or glass frit bonding) may require temperatures ranging from 400 to 1100° C. and may result in the entire packaged device seeing these temperatures during bonding which may cause thermal damage to components. Accordingly, in some examples, components connected to the substrates may be thermally damaged when using heating methods other than laser heating. In some examples, when using laser enhanced bonding methods, the interface may be heated to greater temperatures (e.g., 400 to 1100° C.), but the rest of the packaged device may not since the heating may be localized at the point on which the laser is focused and since the substrates may not conduct heat to the portions of the packaged device outside of the laser heated region.

Furthermore, when substrates are used in a packaged device, the components connected to the substrates may be further insulated from laser heating of the interface since glass substrates may be thermally insulating. Therefore, a packaged device according to the present disclosure including glass substrates may include components that are thermally sensitive. Such components included in the packaged device may even be arranged near the interface on which the laser is directed during bonding without experiencing thermal damage. This may allow for more compact and flexible component layout options within the packaged device of the present disclosure relative to other available packaging options.

The surfaces of planar substrate 102 and recessed substrate 104 that are interfaced with one another may be referred to as "interface surfaces" of substrates 102, 104. The interface surface of planar substrate 102 may be a portion of interior surface 118 near the perimeter of planar substrate 102 where recessed substrate 104 is brought into contact with planar substrate. The interface surface of recessed substrate 104 may be the flattened surface of rim 138 of recessed substrate 104. In some examples, the flattened surface of rim 138 may not include interface layer 140, e.g., when one of the planar and recessed substrates 102, 104 include silicon substrates. In other examples, the flattened surface of rim 138 may include interface layer 140 (e.g., amorphous silicon) to promote bonding, e.g., when both planar and recessed substrates 102, 104 are glass substrates.

One or both of the interface surfaces may be prepared for direct bonding before placing the interface surfaces in contact with one another. Surface preparation may enable different atoms or molecules of the interface surfaces to attract one another. These attractive forces may create a direct bond between planar substrate 102 and recessed substrate 104. The type of surface preparation performed on the interface surfaces may vary, e.g., based on the chemical composition of substrates 102, 104.

One or both of the interface surfaces may be prepared by polishing to remove surface deformities such as burrs, gouges, ridges, or other irregularities (400). Different techniques may be used to polish the interface surfaces. For example, the interface surfaces may be mechanically polished, chemically polished, or treated by chemical-mechanical polishing (CMP) techniques. The interface surfaces may be polished until the surfaces exhibit comparatively low surface roughness values. Polishing the interface surfaces until the surfaces exhibit comparatively low surface roughness values may enhance direct bond formation. While smoother interface surfaces generally facilitate improved direct bond formation by allowing atoms or molecules of different surfaces to come into close contact, in some examples, comparatively rough surfaces may be bonded together.

In addition to or in lieu of polishing, the interface surfaces may be prepared for direct bonding by cleaning the interface surfaces to remove particles and contaminates from the interface surfaces (402). Cleaning the interface surfaces may include ultrasonic and/or megasonic cleaning. In addition to polishing and cleaning, interface surfaces may be prepared for direct bonding by chemically activating one or both of interface surfaces (404). Chemical activation may promote direct bond formation between the interface surfaces when the interface surfaces are brought into contact with one another. Chemical activation may involve exposing the interface surfaces to a plasma (e.g., nitrogen or oxygen plasma).

Independent of the specific techniques used, after suitably preparing the interface surfaces for direct bonding, the interface surfaces may be brought into contact with each other to establish a direct bond between substrates 102, 104 (406). Heating substrates 102, 104 may, in some examples, promote bond formation between the interface surfaces by providing energy to overcome an activation energy barrier for covalent bond formation (408). In some examples, a direct bond formed between interface surfaces may be optionally heated by directing a laser on at least a portion of the interface (410). The energy provided by the laser may heat the direct bond formed at the interface. Generally, a direct bond between the interface surfaces may hold substrates 102, 104 in a substantially fixed arrangement relative to one another. The direct bond formed between substrates 102, 104 that is heat treated, e.g., using a laser, may exhibit a greater strength than the bond formed prior to heating.

In one implementation of the method described in FIG. 7, planar and recessed substrates 102, 104 may include glass substrates (e.g., borosilicate glass). One of substrates 102, 104 may include a silicon layer (e.g., amorphous silicon) deposited at an interface between substrates 102, 104 prior to bringing substrates 102, 104 into contact with one another. In this implementation, a laser used to heat the interface (e.g., heat the silicon layer) may be selected such that the laser is transmitted through the glass substrate (either substrate 102 or substrate 104) and absorbed by the silicon layer, resulting in a heating of the silicon layer and strengthening of the bond between substrates 102, 104.

In another implementation of the method described in FIG. 7, one of substrates 102, 104 may include a glass substrate (e.g., borosilicate glass) and the other one of substrates 102, 104 may include a semiconductor substrate (e.g., silicon). In this implementation, a laser used to heat the interface (e.g., heat the silicon layer) may be selected such that the laser is transmitted through the glass substrate and absorbed by the semiconductor layer, resulting in a heating of the semiconductor/glass interface and strengthening of the bond between substrates 102, 104.

Figure 8:
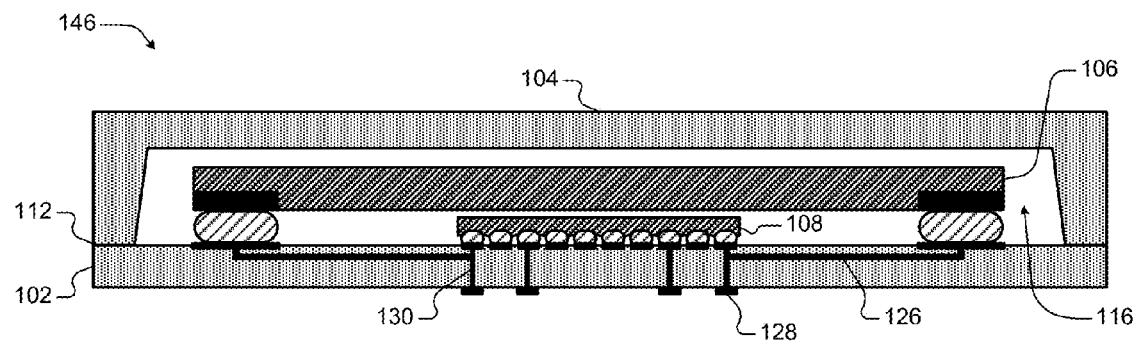
FIG. 8 shows a cross-sectional side view of a bond between two substrates that does not include an additional layer of material.
Figure 11A:
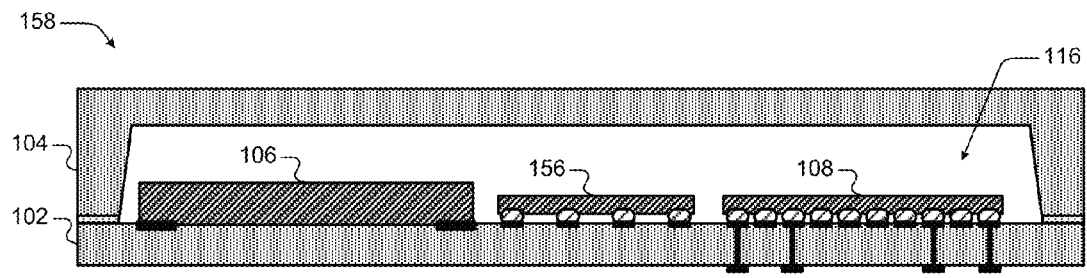
FIGS. 11A-11C show cross-sectional side views of example arrangements of devices that are fabricated directly onto a substrate.
Figure 11B:
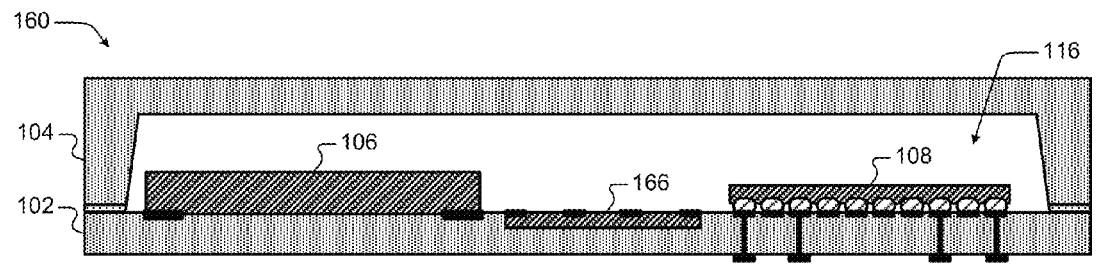
Figure 11C:
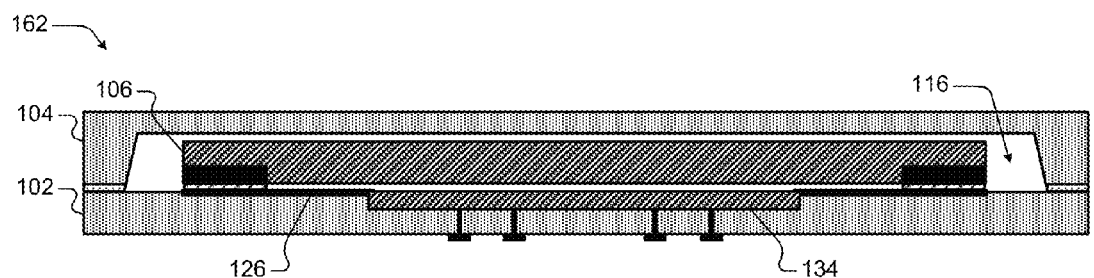
Figure 11D:
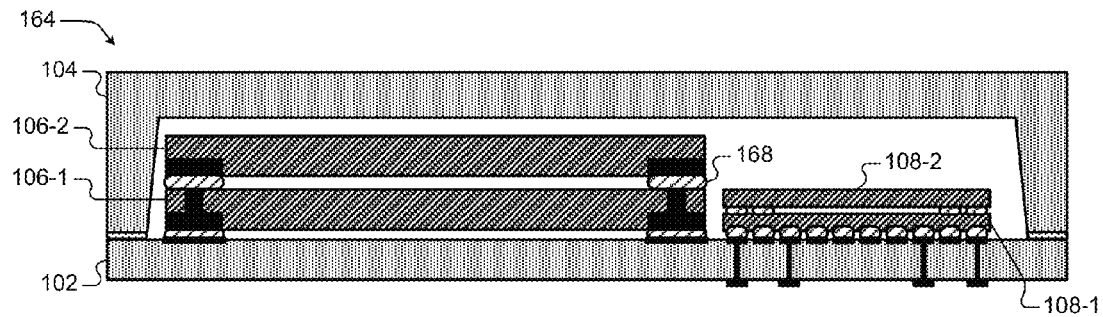
FIG. 11D shows a cross-sectional side view of an example packaged device including stacked dice and stacked energy storage devices.
Figure 12:
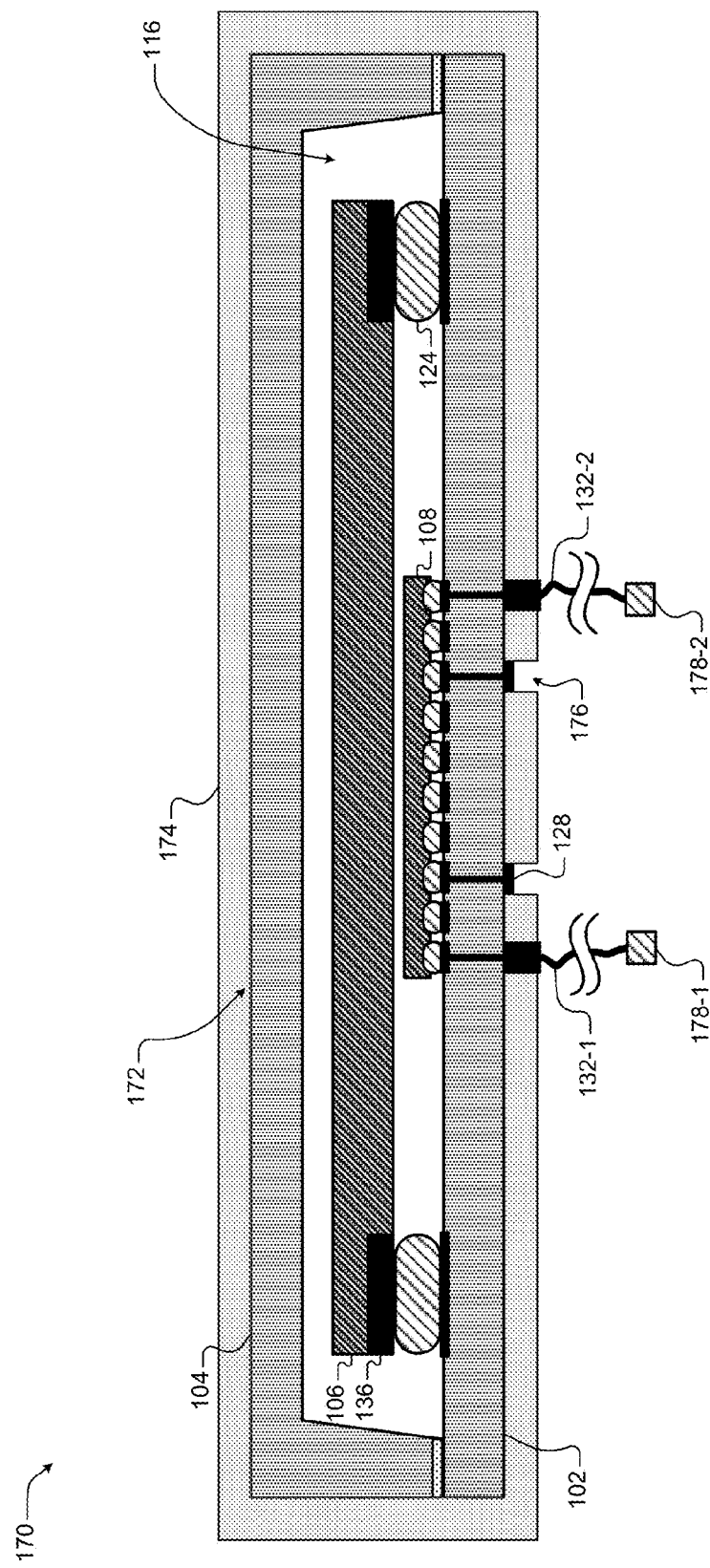
FIG. 12 shows a cross-sectional side view of an encapsulated packaged device.

FIGS. 8-12 illustrate various features of packaged devices of the present disclosure. FIG. 8 illustrates a cross-sectional side view of a bond between planar and recessed substrates 102, 104 that does not include an additional layer of material (e.g., interface layer 140) used in some circumstances to promote bonding between planar and recessed substrates 102, 104. FIG. 9 illustrates a cross-sectional side view of a plurality of dice 142, 144 mounted to planar substrate 102 underneath ESD 106. FIGS. 10A-10C illustrate cross-sectional side views of example packaged devices including various arrangements of adjacent devices. FIGS. 11A-11C illustrate cross-sectional side views of example arrangements of devices that are fabricated directly onto planar substrate 102. FIG. 11D illustrates a cross-sectional side view of an example packaged device including stacked dice and stacked ESDs. FIG. 12 illustrates a cross-sectional side view of encapsulation of an example packaged device that includes leads 132-1, 132-2. Each of FIGS. 8-12 are now discussed in turn.

FIG. 8 shows a packaged device 146 in which interface 112 between planar substrate 102 and recessed substrate 104 does not include an additional layer of material (e.g., interface layer 140) deposited on either planar or recessed substrates 102, 104. In this example, one or both of planar and recessed substrates 102, 104 may include semiconductor substrates, e.g., silicon substrates. For example, one of recessed and planar substrates 102, 104 may be a glass substrate while the other of recessed and planar substrates 102, 104 may be a semiconductor substrate, e.g., a silicon substrate. In another example, both planar and recessed substrates 102, 104 may be semiconductor substrates, e.g., silicon substrates. As described above with respect to FIG. 7, the silicon/glass or silicon/silicon interface between planar and recessed substrates 102, 104 in FIG. 8 may be bonded using a laser assisted bonding technique without addition of interface layer 140 (e.g., the layer of amorphous silicon).

FIG. 9 illustrates a packaged device 148 that is similar to packaged device 100 of FIG. 1, however, packaged device 148 includes more than one die mounted under ESD 106. In FIG. 9, ESD 106 straddles two dice 142, 144 that are mounted to planar substrate 102. Although two dice 142, 144 are illustrated as mounted under ESD 106 in FIG. 9, more than two dice may be mounted under ESD 106 in other examples.

Packaged device 148 also differs from packaged device 100 in FIG. 1 in that packaged device 148 of FIG. 9 does not include package vias 130. For example, packaged devices, used for some sensing applications, that include sensors such as temperature, pressure, accelerometers, and gyroscopic sensors may not require an electrical interface with the patient provided by external pads 128. In other words, sensors such as temperature, pressure, accelerometers, and gyroscopic sensors may monitor physiological parameters of the patient, such as patient temperature, blood pressure, patient activity, and patient orientation, while enclosed within a package. Integrated circuits included in such packages may transmit the data indicating the physiological parameters via an antenna included in package 148, for example. In other example, an optical transceiver included in package 148 may also monitor physiological parameters of the patient while enclosed within a packaged device when one or both of substrates 102, 104 is transparent to the wavelength of light emitted from the transceiver. Subsequently, integrated circuits included in packaged device 148 may transmit, via an antenna, the physiological parameters determined based on data from the optical transceiver.

In summary, when packaged device 148 is configured for a sensor application, example components included in packaged device 148 may include a sensor (e.g., a temperature sensor, accelerometer, gyroscopic sensor, and/or optical transceiver) fabricated on one of dice 142, 144, an antenna fabricated on dice 142, 144, and an integrated circuit fabricated on one of dice 142, 144. The integrated circuit may be configured to receive signals from the sensor, determine a physiological parameter of the patient (e.g., patient posture), and transmit the patient posture data to an external device via the antenna included in packaged device 148. Although not illustrated in FIG. 9, conductive traces may provide connection between ESD 106, die 142, and die 144.

FIGS. 10A-10C illustrate various packaged devices 150, 152, 152 including ESD 106 and dice 108, 156. The various representations of dice (e.g., numbers and illustrations) described in the present disclosure (e.g., dice 108, 142, 144, 156) are used for illustration purposes only, and are not intended to imply similar or different functionality between the dice. For example, dice 108, 142, 144, 156 may include any of the functionality described in the present disclosure, and similarities in illustration and numbering are not meant to imply similar functionality.

In FIG. 10A, packaged device 150 includes ESD 106 located alongside a single die 108 mounted on planar substrate 102. In FIG. 10B, packaged device 152 includes ESD 106 located at an edge of packaged device 152 alongside two dice 108, 156 mounted on planar substrate 102. Although ESD 106 is illustrated alongside two dice 108, 156, ESD 106 may be located alongside more than two dice in some examples. In other examples, ESD 106 may straddle one or more dice (as illustrated in FIG. 9) and additionally, ESD 106 that is straddling two dice may be adjacent to additional dice mounted on planar substrate 102.

FIG. 10C illustrates ESD 106 centrally located within packaged device 154. In this example, dice 108, 156 are located near interface 112 between planar and recessed substrates 102, 104. Any heat generated in planar and recessed substrates 102, 104 during bonding (e.g., due to heating by the laser) may be localized near interface 112 of planar and recessed substrates 102, 104, and therefore, a central location of ESD 106 within cavity 116 and away from interface 112 may provide additional insulation between heat generated during bonding and ESD 106. Thus, when centrally located within package 154, ESD 106 may be insulated from heat generated during bonding, and therefore incur a reduced chance of thermal damage.

FIGS. 11A-11C illustrate packaged devices 158, 160, 162 that include devices fabricated directly on planar substrate 102. In FIG. 11A, ESD 106 is fabricated directly on planar substrate 102, as opposed to connected to planar substrate 102 using solder bumps 124. For example, ESD 106 fabricated directly on planar substrate 102 may include a battery, such as a solid state battery, or a capacitor. Adjacent to ESD 106 fabricated directly on planar substrate 102 are located dice 108, 156 which are mounted on planar substrate 102. Accordingly, in some example packaged devices of the present disclosure, some devices included in a packaged device may be fabricated directly on a substrate of the packaged device while other devices in the packaged device may be fabricated on dice and subsequently mounted along with the devices fabricated directly on the substrate.

FIG. 11B includes an integrated device 166, such as an integrated circuit, sensor, or antenna fabricated on planar substrate 102. When planar substrate 102 is cut from a silicon wafer, integrated device 166 may be an integrated circuit, sensor, or antenna fabricated on or within planar substrate 102 using various semiconductor processing techniques. In examples where planar substrate 102 is a glass material (e.g., borosilicate glass), devices (e.g., integrated device 166) such as integrated circuits, sensors, and antennae may also be built up on the glass in thin film layers.

FIG. 11C illustrates a packaged device 162 that includes integrated device 134 fabricated on planar substrate 102 with ESD 106 straddling integrated device 134. Integrated device 134 may include an integrated circuit, sensor, and/or antenna integrated into planar substrate 102, for example. This configuration of devices included in packaged device 162 may optimize the usage of cavity 116 within packaged device 162. For example, integrated device 134 that is integrated into planar substrate 102 may represent an implementation of a packaged device that uses a least amount of space within cavity 116 for packaging devices. Therefore, a maximum amount of space in cavity 116 may be reserved for ESD 106, allowing for a maximum amount of energy storage per unit volume within packaged device 162. Thus, the usable lifetime of packaged device 162, based on battery life (e.g., when ESD 106 is a battery), may be maximized in packaged device 162 that allows for maximizing the size of ESD 106 per unit volume of packaged device 162.

In example packaged device 162 of FIG. 11C, ESD 106 is mounted to planar substrate 102 over top of integrated device 134. Although ESD 106 is illustrated as straddling integrated device 134, in some examples, integrated device 134 may be fabricated along the entire length of planar substrate 102 that defines cavity 116, and ESD 106 may contact bonding pads 122 within the perimeter of integrated device 134.

With reference to FIGS. 14A-14B, in some examples, a packaged device (e.g., packaged devices 201, 203) may include ESD 106 (e.g., a battery) fabricated in recessed region 110. Subsequent to fabrication of ESD 106 in recessed region 110, the combined ESD 106 and recessed substrate 104 may be connected to planar substrate 102. For example, the combined recessed substrate 104 and ESD 106 may be brought into contact with planar substrate 102 and bonding pads 122, respectively. Solder material on ESD contacts 136 may then be melted to form solder bumps 124, and planar and recessed substrates 102, 104 may be bonded (e.g., using laser enhanced bonding) to hermetically enclose ESD 106 between planar and recessed substrates 102, 104. Packaged device 201 of FIG. 14A, in which ESD 106 is fabricated within recessed region 110, may eliminate cavity 116, or at least minimize an amount of empty space enclosed within packaged device 201. Accordingly, packaged device 201 of FIG. 14A may provide a more optimized energy storage per unit volume solution than packaged devices including empty space in cavity 116. Although a space is illustrated in FIG. 14A between ESD 106 and planar substrate 102, in some examples, as illustrated in FIG. 14B, ESD 106 may be mounted nearly flush with planar substrate 102, further minimizing (e.g., substantially eliminating) any empty space within packaged device 203.

FIG. 11D illustrates stacking of devices in packaged device 164. Packaged device 164 includes stacked ESDs 106-1, 106-2 and stacked dice 108-1, 108-2. Stacking of ESDs 106-1, 106-2 and dice 108-1, 108-2 may reduce the total area (i.e. footprint) of a packaged device relative to other packaged devices that include ESDs 106-1, 106-2 and dice 108-1, 108-2 arranged in an un-stacked configuration on planar substrate 102. Dice 108-1, 108-2 may be stacked and interconnected outside of packaged device 164 and then mounted as a single unit within packaged device 164 in some examples. In other examples, die 108-1 may be mounted in packaged device 164 and then die 108-2 may be stacked on die 108-1. Dice 108-1, 108-2 may be interconnected using through-silicon vias, for example. ESDs 106-1, 106-2 may also be stacked and interconnected outside of packaged device 164 and then mounted in packaged device 164, or alternatively ESDs 106-1, 106-2 may be stacked one at a time within packaged device 164. ESDs 106-1, 106-2 may be electrically connected through interconnects 168 illustrated in FIG. 11D. Interconnects 168 may include through-substrate vias.

FIG. 12 illustrates an encapsulated device 170 including a packaged device 172 covered with an encapsulation 174. Encapsulation 174 may improve the biocompatibility of packaged device 172, and therefore enhance the suitability of packaged device 172 for implantation into a patient. Encapsulation 174 may include, for example, a silicone coating over packaged device 172, a titanium layer over packaged device 172, or a silicone layer coated in titanium. Encapsulation 174 defines openings 176 through which external pads 128 are accessible. External pads 128 may be nearly flush with exterior surface 120 of planar substrate 102 in some examples. In other examples, instead of external pads 128, leads 132-1, 132-2 (collectively "leads 132") may be electrically connected through package vias 130 to devices (e.g., integrated circuits) housed within cavity 116. As illustrated in FIG. 12, leads 132-1, 132-2 may include electrodes 178-1, 178-2, respectively. Electrodes 178-1, 178-2 (collectively "electrodes 178") may be used for sensing electrical physiological signals in some examples. For example, integrated circuits in packaged device 172 may sense ECG, IEGM, and EEG signals via external pads 128 and/or electrodes 178. In other examples, electrodes 178 may be used for delivering electrical stimulation to the patient. For example, integrated circuits in packaged device 172 may deliver cardiac pacing stimulation or electrical neurostimulation, depending on the application in which encapsulated device 170 is used.

Although two external pads 128 and two leads 132-1, 132-2 are illustrated in FIG. 12, in some examples, a greater or lesser number of external pads 128 and leads 132 may be connected to packaged device 172. In some examples, packaged device 172 may not include any external pads 128 or leads 132, but instead, encapsulation 174 may cover the entire exterior of packaged device 172. In other examples, packaged device 172 may not include external pads 128, but may instead include leads 132. In other examples, packaged device 172 may not include leads 132, but may include external pads 128.

The number of external pads 128 and leads 132 may vary based on the application in which packaged device 172 is used. In examples where packaged device 172 is used for cardiac pacing, packaged device 172 may include one or more external pads 128 and leads 132. For example, an external pad 128 on packaged device 172 may serve as a reference electrode, while one or more leads 132 may serve as stimulation electrodes that deliver cardiac pacing stimulation to one or more chambers of the patient's heart.

In examples where packaged device 172 is used for neurostimulation, an external pad 128 on packaged device 172 may serve as a reference electrode, while one or more leads 132 may serve as neurostimulation electrodes that provide electrical therapy according to a program (e.g., including amplitude, pulse width, and pulse rate) stored within an integrated circuit of packaged device 172. In the case of neurostimulation, a plurality of leads, e.g., 8, 16, 24, or more leads may be used to provide stimulation. In some examples, the plurality of leads may be wrapped within separate sheaths that house the separate leads 132 and electrodes 178 and extend outward from packaged device 172 to a target stimulation location within the patient. In other examples, packaged device 172 may deliver leadless stimulation using a plurality of external pads 128 arranged on the exterior of packaged device 172 at a target stimulation site. Although 8, 16, 24, or more leads 132 may be used for neurostimulation applications, the number of external pads 128 and/or leads 132 may only be limited by the size of external pads 128 and/or leads 132, and the size of the substrate through which external pads 128 and leads 132 are attached.

As an alternative to coating packaged device 172 in encapsulation 174, packaged device 172 may be enclosed in a biocompatible package, such as a titanium sleeve. When enclosed in such a package, leads 132 may be fed through an opening in the package to the target stimulation site.

FIGS. 13A-13E are functional block diagrams of example packaged devices including modules that represent functionality that may be included in packaged devices according to the present disclosure. Modules included within packaged devices of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Memory may include any volatile, non-volatile, magnetic, or electrical media, such as a random access memory (RAM), read-only memory (ROM), non-volatile RAM (NVRAM), electrically-erasable programmable ROM (EE-PROM), Flash memory, or any other memory device. Furthermore, memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects and does not necessarily imply that such modules or units must be realized by separate hardware or software components. Rather, functionality associated with one or more modules may be performed by separate hardware or software components, or integrated within common or separate hardware or software components.

Modules of the packaged devices of FIGS. 13A-13E may be implemented by one or more devices included on one or more dice mounted in the packaged devices. Additionally, or alternatively, modules of the packaged devices of FIGS. 13A-13E may be implemented by one or more devices integrated into a substrate (e.g., planar substrate 102) of the packaged devices.

Each packaged device of FIGS. 13A-13E includes ESD 106 and a control module 180. ESD 106 illustrated in FIGS. 13A-13E represents ESD 106 as illustrated in the figures preceding FIGS. 13A-13E. ESD 106 may provide power to modules included in the packaged devices of FIGS. 13A-13E. For example, ESD 106 may provide operational power to control module 180, sensor module 182, tissue conduction communication (TCC) module 184, optical receiver 186, optical transmitter 188, and therapy/communication module 190.

Control module 180 may represent any analog/digital circuit included in a packaged device that provides the functionality assigned to control module 180 herein. For example, control module 180 may represent an integrated circuit that is configured to provide analog electronic functions such as signal conditioning (e.g., filtering and amplification). Control module 180 may also represent an integrated circuit that provides logic functions and data storage functions. Control module 180 may be implemented on one or more dice included in a packaged device, and, additionally or alternatively, may be implemented as an integrated circuit fabricated on planar substrate 102.

Figure 13A:
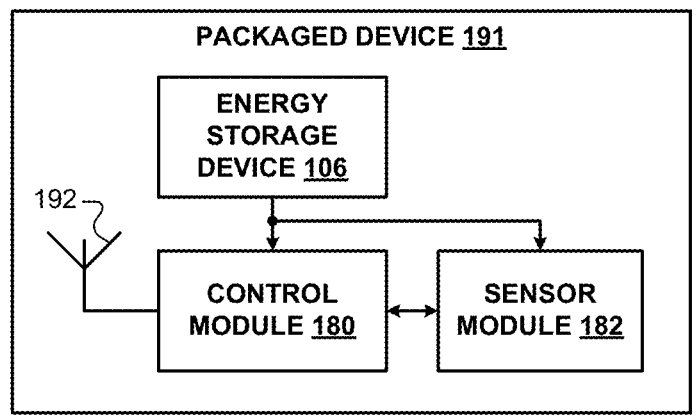
FIGS. 13A-13E are functional block diagrams illustrating exemplary packaged devices that include features that may be included in packaged devices according to the present disclosure.

Referring now to FIG. 13A, packaged device 191 includes ESD 106, control module 180, sensor module 182, and an antenna 192. Antenna 192 may represent an antenna included in packaged device 191, e.g., fabricated on a die mounted in packaged device 191 or fabricated on one of planar or recessed substrate 102, 104 of packaged device 191. Sensor module 182 may represent a sensor included in packaged device 191. In some examples, sensor module 182 may include at least one of an accelerometer, a gyroscopic sensor, a magnetic field sensor, and a temperature sensor.

Packaged device 191 of FIG. 13A may provide a sensing function when implanted in a patient. Sensor module 182 may generate signals that indicate sensed physiological parameters of the patient. Control module 180 may determine physiological parameters of the patient based on signals received from sensor module 182. In one example, when sensor module 182 includes an accelerometer (e.g., including one or more axes), control module 180 may determine physiological parameters of the patient, including, but not limited to, a posture of the patient and/or an activity level of the patient based on signals received from the accelerometer. Subsequently, control module 180 may wirelessly transmit data including the determined physiological parameters via antenna 192. For example, control module 180 may wirelessly transmit data to another implanted medical device within the patient or to an external device, such as a patient programming device used to program neurostimulator therapy programs and/or cardiac pacing parameters.

Packaged devices may communicate with a programming device such as a handheld computing device, desktop computing device, or a networked computing device using an antenna and/or using tissue conductance communication. The programming device may be used by a clinician to program components of packaged devices, e.g., for cardiac electrical therapy and/or neurostimulation electrical therapy. Additionally, the packaged devices may upload measured physiological data to the programming device. In some examples, this disclosure contemplates a system that includes one or more of the packaged devices described herein and one or more programming devices to program components of packaged devices.

Figure 13B:
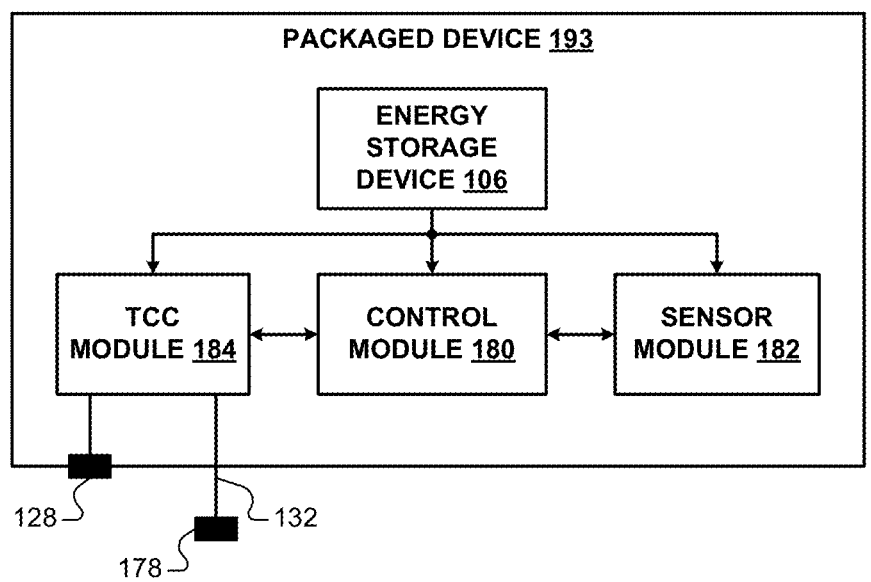

FIG. 13B illustrates a packaged device 193 that includes ESD 106, control module 180, and sensor module 182 that operate as described above. However, packaged device 193 includes TCC module 184 in place of antenna 192. TCC module 184 may enable tissue conductance communication. For example, TCC module 184 may transmit data to devices implanted in the patient, or in contact with the patient, via external electrodes 128, 178. Accordingly, control module 180 of packaged device 193 may determine physiological parameters of the patient (e.g., patient posture and/or activity) and TCC module 184 may transmit the determined physiological parameters to other devices implanted in the patient, or in contact with the patient. Additionally, TCC module 184 may receive signals transmitted by other devices implanted in patient, or in contact with the patient, via external electrodes 128, 178, and control module 180 may receive data from TCC module 184 derived from the signals.

Figure 13C:
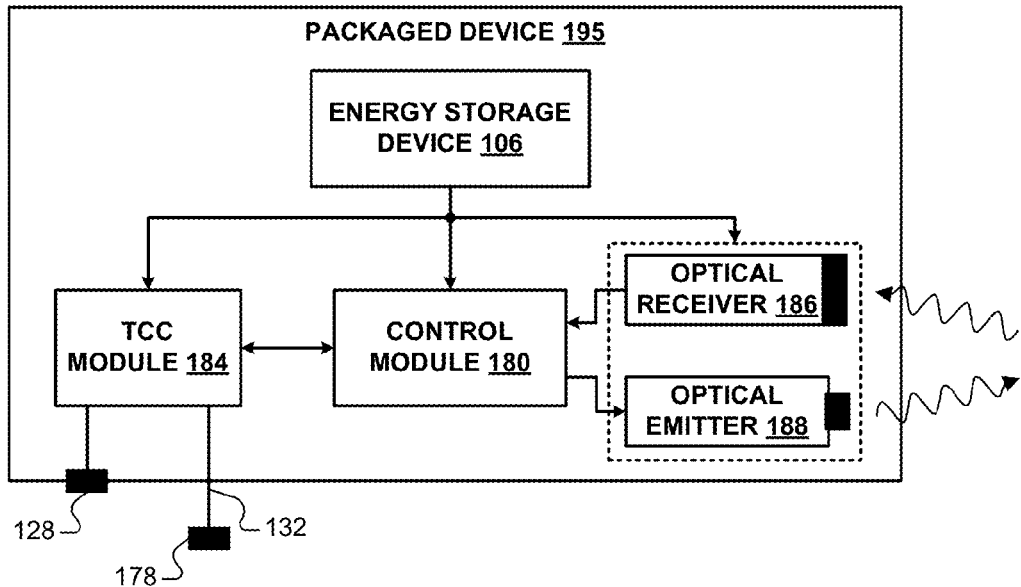

Referring now to FIG. 13C, a packaged device 195 includes ESD 106, control module 180, and TCC module 184. Additionally, packaged device 195 includes components of an optical transceiver. The optical transceiver includes an optical emitter 186 and an optical receiver 188. Optical emitter 188 and/or optical receiver 186 may be included on a die mounted in packaged device 195 and/or fabricated onto planar substrate 102. Optical emitter 188 may emit light through planar and/or recessed substrates 102, 104. Optical receiver 186 may receive reflected portions of the emitted light. Control module 180 may determine physiological parameters based on the received light, such as changes in metabolite levels in the blood, such as oxygen saturation levels or glucose level, or changes in tissue perfusion. TCC module 184 may then transmit the physiological parameters determined by control module 180 via tissue conduction communication.

Figure 13D:
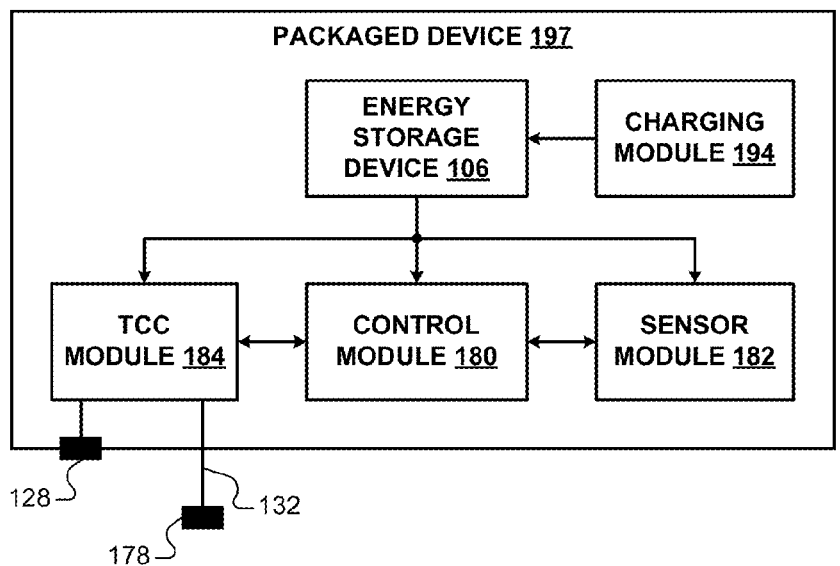

Referring now to FIG. 13D, packaged device 197, having similar functionality as packaged device 193, includes a charging module 194. Charging module 194 may represent a device included in packaged device 197 that functions to charge ESD 106. For example, charging module 194 may include a piezoelectric device, betavoltaic source, or a photovoltaic source.

Figure 13E:
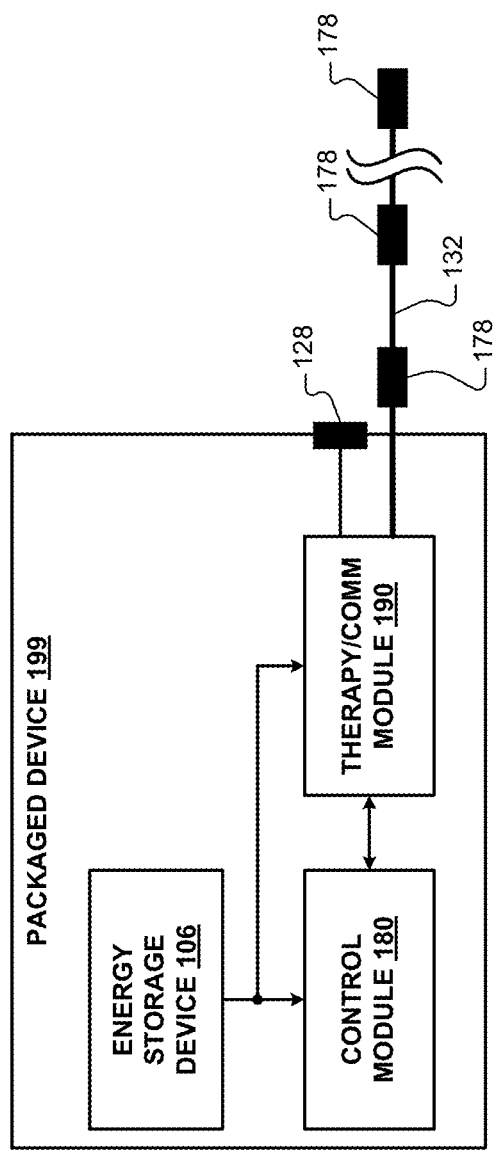

Referring now to FIG. 13E, packaged device 199 includes a therapy/communication module 190. Therapy/communication module 190 may perform various functions related to therapy delivery and tissue conductance communication. Therapy/communication module 190 may be connected to one or more external pads 128 and/or one or more electrodes 178 on leads 132. In one example, therapy/communication module 190 may transmit and receive data through tissue conduction communication using external pads 128 and/or one or more of electrodes 178. In other examples, therapy/communication module 190 may provide electrical stimulation therapy via external pads 128 and/or electrodes 178.

In some examples, electrical stimulation therapy may include neurostimulation therapy. In these examples, therapy/communication module 190, under control of control module 180, may provide neurostimulation therapy via external pads 128 and/or electrodes 178. Therapy/communication module 190 may deliver electrical stimulation therapy via one or more of leads 132 that include electrodes 178 implanted proximate to target locations associated with, for example, the brain, the spinal cord, pelvic nerves, peripheral nerves, or the gastrointestinal tract of a patient. Hence, stimulation provided by packaged device 199 may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, e.g., functional electrical stimulation (FES), to promote muscle movement or prevent atrophy.

In other examples, packaged device 199 may provide functionality similar to that of an implantable pacemaker, or a cardioverter-defibrillator. In these examples, therapy/communication module 190, under control of control module 180, may provide cardiac sensing and pacing functions. In a cardiac electrical therapy application, leads 132 may extend into the heart of the patient and electrodes 178 may connect to the right ventricle of the heart, the left ventricle of the heart, and/or the right atrium of the heart. Using this electrode configuration, therapy/communication module 180 may sense electrical activity of the heart and/or deliver electrical stimulation (e.g., pacing pulses) to the heart using external pads 128 and/or electrodes 178 on leads 132.

Although packaged devices according to the present disclosure are described above for use in medical applications, the packaged devices of the present disclosure are not limited to medical applications, but instead it is contemplated that the packaged devices may also be used in general electronics applications. For example, the packaged devices may include integrated circuits, sensors, and other components that are not directed to medical applications, but are directed to general sensing applications, information processing applications (e.g., analog signal processing and digital information processing), and data storage applications (e.g., memory). In some medical or non-medical applications, the packaged devices may be mounted on other integrated devices (e.g., an integrated die) and packaged together with the integrated devices in a multi-chip package, or the packaged devices may be connected to a printed circuit board, for example.

Although the packaged devices according to the present disclosure are described as including the components on one of the two substrates that comprise the packaged devices, in some examples, both substrates of a packaged device according to the present disclosure may include components, such as sensors and integrated circuits, e.g., fabricated on dice connected to either substrate or fabricated directly on the substrates. In examples where both substrates include components, the components included on separate substrates may be electrically interconnected, for example, through the interface between the substrates.

Various examples have been described. These and other examples are within the scope of the following claims.

The invention claimed is:

1. A medical device comprising:
   a first substrate that includes at least one of a first semiconductor material and a first insulating material;
   a second substrate that includes at least one of a second semiconductor material and a second insulating material, a first major surface of the second substrate bonded to the first substrate such that the first and second substrates define a first enclosed cavity between the first and second substrates;
   a third substrate that includes at least one of a second semiconductor material and a second insulating material, the third substrate bonded to a second major surface of the second substrate such that the second and third substrates define a second enclosed cavity between the second and third substrates;
   an encapsulant cover disposed over outer surfaces of the first and third surfaces to seal the device;
   a control module disposed within at least one of the first enclosed cavity and the second enclosed cavity, the control module configured to at least one of:
      determine a physiological parameter of a patient and deliver electrical stimulation to the patient; and
   an energy storage device disposed within at least one of the first enclosed cavity and the second enclosed cavity configured to supply power to the control module.

2. The medical device of claim 1, wherein the first and second substrates comprise glass substrates.

3. The medical device of claim 2, further comprising a silicon layer deposited within the bond between the first and second substrates.

4. The medical device of claim 2, further comprising a light absorbing layer deposited within the bond between the first and second substrates, wherein the light absorbing layer absorbs light at a wavelength that is transmitted by one of the first and second substrates.

5. The medical device of claim 1, wherein the first and second substrates comprise semiconductor substrates.

6. The medical device of claim 1, wherein one of the first and second substrates comprises a glass substrate, and wherein the other one of the first and second substrates comprises a semiconductor substrate.

7. The medical device of claim 1, wherein the thickness of the device including the thickness of the first and second substrates and the depth of each of the first enclosed cavity and the second enclosed cavity is less than 3 millimeters.

8. The medical device of claim 1, wherein at least a portion of the control module is disposed on a die, and wherein the die is mounted to one of the first and second substrates.

9. The medical device of claim 1, wherein at least a portion of the control module is fabricated into one of the first and second substrates.

10. The medical device of claim 1, further comprising a sensor housed within one of the first enclosed cavity and the second enclosed cavity.

11. The medical device of claim 10, wherein the sensor includes one of a temperature sensor, a pressure sensor, an accelerometer, and a gyroscopic sensor, and wherein the control module determines at least one of a temperature of the patient, a pressure within the patient, an activity level of the patient, and a posture of the patient based on signals received from the sensor.

12. The medical device of claim 1, further comprising an antenna, wherein the control module at least one of transmits and receives data via the antenna.

13. The medical device of claim 1, wherein the energy storage device includes one of a battery and a capacitor.

14. The medical device of claim 13, wherein the energy storage device includes a solid state battery.

15. The medical device of claim 1, further comprising an electrical connection that extends from the control module through one of the first and second substrates to an external surface of the device.

16. The medical device of claim 15, wherein the control module is configured to provide electrical stimulation to the patient via the electrical connection.

17. The medical device of claim 16, wherein the electrical stimulation includes one of cardiac electrical stimulation and neurostimulation.

18. The medical device of claim 15, wherein the control module is configured to monitor electrical physiological signals of the patient via the electrical connection.

19. The medical device of claim 1, wherein the energy storage device is formed within a recess defined by one of the first and third substrates.

20. The medical device of claim 1, further comprising an external pad for coupling the control module to a second medical device.

* * * * *